(12) United States Patent
Deisseroth et al.

(10) Patent No.: US 9,274,099 B2
(45) Date of Patent: Mar. 1, 2016

(54) SCREENING TEST DRUGS TO IDENTIFY THEIR EFFECTS ON CELL MEMBRANE VOLTAGE-GATED ION CHANNEL

(75) Inventors: Karl Deisseroth, Palo Alto, CA (US); Feng Zhang, Stanford, CA (US); Viviana Gradinaru, Palo Alto, CA (US); M. Bret Schneider, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 12/187,927

(22) Filed: Aug. 7, 2008

(65) Prior Publication Data

US 2009/0099038 A1  Apr. 16, 2009

Related U.S. Application Data

(63) Continuation-in-part of application No. 11/651,422, filed on Jan. 9, 2007, now Pat. No. 8,926,959, which is a continuation-in-part of application No. 11/459,636, filed on Jul. 24, 2006, now Pat. No. 8,906,360.

(60) Provisional application No. 60/955,116, filed on Aug. 10, 2007, provisional application No. 60/701,799, filed on Jul. 22, 2005.

(51) Int. Cl.
| | |
|---|---|
| *A61N 5/06* | (2006.01) |
| *G01N 33/50* | (2006.01) |
| *C40B 60/12* | (2006.01) |
| *G01N 33/68* | (2006.01) |

(52) U.S. Cl.
CPC .......... *G01N 33/5008* (2013.01); *A61N 5/0622* (2013.01); *C40B 60/12* (2013.01); *G01N 33/6872* (2013.01); *B01J 2219/00315* (2013.01); *B01J 2219/00495* (2013.01); *B01J 2219/00702* (2013.01)

(58) Field of Classification Search
CPC .. C07K 14/705; C07K 14/47; G01N 2500/00; G01N 2500/10; G01N 33/582; G01N 33/52; G01N 33/5008; G01N 33/6872; C12Q 2600/136; C12Q 2563/107; A61N 5/0622; C40B 60/12; B01J 2219/00702; B01J 2219/00315; B01J 2219/00495
See application file for complete search history.

(56) References Cited

U.S. PATENT DOCUMENTS

| | | | |
|---|---|---|---|
| 2,968,302 A | 1/1961 | Fry et al. | |
| 3,131,690 A | 5/1964 | Innis et al. | |
| 3,499,437 A | 3/1970 | Balamuth et al. | |
| 3,567,847 A | 3/1971 | Price | |
| 4,343,301 A | 8/1982 | Indech | |
| 4,559,951 A | 12/1985 | Dahl et al. | |
| 4,616,231 A | 10/1986 | Autrey et al. | |
| 4,865,042 A | 9/1989 | Umemura et al. | |
| 4,879,284 A | 11/1989 | Land et al. | |
| 5,032,123 A | 7/1991 | Katz et al. | |
| 5,041,224 A * | 8/1991 | Ohyama et al. | 210/500.27 |
| 5,082,670 A | 1/1992 | Gage et al. | |
| 5,249,575 A | 10/1993 | Di Mino et al. | |
| 5,267,152 A | 11/1993 | Yang et al. | |
| 5,290,280 A | 3/1994 | Daikuzono et al. | |
| 5,330,515 A | 7/1994 | Rutecki et al. | |
| 5,382,516 A | 1/1995 | Bush | |
| 5,445,608 A | 8/1995 | Chen et al. | |
| 5,460,950 A | 10/1995 | Barr et al. | |
| 5,460,954 A | 10/1995 | Lee et al. | |
| 5,470,307 A | 11/1995 | Lindall | |
| 5,495,541 A | 2/1996 | Murray et al. | |
| 5,520,188 A | 5/1996 | Hennige et al. | |
| 5,527,695 A | 6/1996 | Hodges et al. | |
| 5,550,316 A | 8/1996 | Mintz | |
| 5,641,650 A | 6/1997 | Turner et al. | |
| 5,703,985 A | 12/1997 | Owyang et al. | |
| 5,722,426 A | 3/1998 | Kolff | |
| 5,738,625 A | 4/1998 | Gluck | |
| 5,739,273 A | 4/1998 | Engelman et al. | |

(Continued)

FOREIGN PATENT DOCUMENTS

| | | |
|---|---|---|
| CN | 1079464 A | 12/1993 |
| EP | 1 334 748 | 8/2003 |

(Continued)

OTHER PUBLICATIONS

Rivera et al., 2002, The Journal of Cell Biology, 159: 747-752.*

(Continued)

*Primary Examiner* — Thaian N Ton
*Assistant Examiner* — Titilayo Moloye
(74) *Attorney, Agent, or Firm* — Bozicevic, Field & Francis LLP; Paula A. Borden

(57) ABSTRACT

A variety of applications, systems, methods and constructs are implemented for use in connection with screening of ion-channel modulators. Consistent with one such system, drug candidates are screened to identify their effects on cell membrane ion channels and pumps. The system includes screening cells having light responsive membrane ion switches, voltage-gated ion switches and fluorescence producing voltage sensors. A chemical delivery device introduces the drug candidates to be screened. An optical delivery device activates the light responsive ion switches. An optical sensor monitors fluorescence produced by the voltage sensors. A processor processes data received from the optical sensor. A memory stores the data received from the optical sensor.

19 Claims, 8 Drawing Sheets

(56) References Cited

U.S. PATENT DOCUMENTS

| | | |
|---|---|---|
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,898,058 A | 4/1999 | Nichols |
| 5,939,320 A | 8/1999 | Littman et al. |
| 6,057,114 A * | 5/2000 | Akong et al. ............... 435/7.21 |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,696,722 B2 | 4/2014 | Deisseroth et al. |
| 8,815,582 B2 | 8/2014 | Deisseroth et al. |
| 8,906,360 B2 | 12/2014 | Deisseroth et al. |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0068202 A1 | 4/2004 | Hansson et al. |
| 2004/0073278 A1 | 4/2004 | Pachys |
| 2004/0076613 A1 | 4/2004 | Mazarakis et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1* | 9/2005 | Hegemann et al. ............... 435/4 |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | De Charms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |

(56) References Cited

U.S. PATENT DOCUMENTS

| | | |
|---|---|---|
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0234273 A1 | 9/2010 | Boyden et al. |
| 2011/0021970 A1 | 1/2011 | Vo-Dinh et al. |
| 2011/0092800 A1 | 4/2011 | Yoo et al. |
| 2011/0105998 A1 | 5/2011 | Deisseroth et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Deisseroth et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0253261 A1 | 10/2012 | Poletto et al. |
| 2013/0030275 A1 | 1/2013 | Seymour et al. |
| 2013/0144359 A1 | 6/2013 | Kishawi et al. |
| 2015/0112411 A1 | 4/2015 | Beckman et al. |

FOREIGN PATENT DOCUMENTS

| | | |
|---|---|---|
| EP | 1873566 A2 | 1/2008 |
| JP | 06-295350 | 10/1994 |
| JP | 2006-295350 | 10/1994 |
| JP | 2010227537 A | 10/2010 |
| WO | WO 96/32076 | 10/1996 |
| WO | WO 00/27293 | 5/2000 |
| WO | WO 01-25466 | 4/2001 |
| WO | WO 03/016486 | 2/2003 |
| WO | WO 03/106486 A2 | 2/2003 |
| WO | WO 2013/016486 | 2/2003 |
| WO | WO 03-040323 | 5/2003 |
| WO | WO 03-040323 * | 5/2003 |
| WO | WO 03-084994 | 10/2003 |
| WO | WO 03-084994 | 10/2003 |
| WO | WO 03-102156 | 12/2003 |
| WO | WO 2004033647 A2 * | 4/2004 |
| WO | WO 2007-024391 | 3/2007 |
| WO | WO 2007-131180 | 11/2007 |
| WO | WO 2008/086470 A1 | 7/2008 |
| WO | WO 2008/106694 | 9/2008 |
| WO | WO 2009/025819 | 2/2009 |
| WO | WO2009/119782 | 10/2009 |
| WO | WO 2009-131837 | 10/2009 |
| WO | WO 2010/006049 | 1/2010 |
| WO | WO 2010/011404 A3 | 1/2010 |
| WO | WO 2010/056970 | 5/2010 |
| WO | WO-2010123993 | 10/2010 |
| WO | WO 2011/005978 | 1/2011 |
| WO | WO 2011/066320 A3 | 6/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/126521 | 8/2013 |
| WO | WO 2013/142196 | 9/2013 |

OTHER PUBLICATIONS

Khosravani et al., 2006, Physiol. Rev. 86: 941-966.*
Aebischer, Patrick, et al. 1991. Long-Term Cross-Species Brain Transplantation of a Polymer-Encapsulated Dopamine-Secreting Cell Line. *Exp Neurol.* 111: 269-275.
Banghart, Matthew, et al. 2004. Light-activated ion channels for remote control of neuronal firing. *Nat. Neurosci.* 7(12): 1381-1386.
Bi, Guo-qiang, et al. 1998. Synaptic Modifications in Cultured Hippocampal Neurons: Dependence on Spike Timing, Synaptic Strength, and Postsynaptic Cell Type. *J. Neurosci.*18(24): 10464-10472.
Bi, Anding, et al. 2006. Ectopic Expression of a Microbial-Type Rhodopsin Restores Visual Responses in Mice with Photoreceptor Degeneration. *Neuron.*50: 23-33.
Boyden, Edward S., et al. 2005. Millisecond-timescale, genetically targeted optical control of neural activity. *Nat. Neurosci.* 8(9): 1263-8.
Callaway, Edward M., et al. 1993. Photostimulation using caged glutamate reveals functional circuitry in living brain slices. *Proc. Natl. Acad. Sci. USA.* 90: 7661-7665.
Dalva, Matthew B. et al. 1994. Rearrangements of Synaptic Connections in Visual Cortex Revealed by Laser Photostimulation. *Science.* 265: 255-258.
Date, Isao, et al. Grafting of Encapsulated Dopamine-Secreting Cells in Parkinson's Disease: Long-Term Primate Study. *Cell Transplant.* 9: 705-709.
Denk, W., et al. 1994. Anatomical and functional imaging of neurons using 2-photon laser scanning microscopy. *J. Neurosci Methods.* 54: 151-162.
Ditterich, Jochen, et al. 2003. Microstimulation of visual cortex affects the speed of perceptual decisions. *Nat. Neurosci.* 6(8): 891-898.
Dittgen, Tanjew, et al. 2004. Lentivirus-based genetic manipulations of cortical neurons and their optical and electrophysiological monitoring in vivo. *PNAS.* 101(52): 18206-11.
Emerich, Dwaine F., et al. 1992. A Novel Approach to Neural Transplantation in Parkinson's Disease: Use of Polymer-Encapsulated Cell Therapy. *Neuroscience and Biobehavioral Reviews.* 16: 437-447.
Farber, Ira C., et al. 1983. Identification of Presynaptic Neurons by Laser Photostimulation. *Science.*222(4627): 1025-1027.
Feng, Guoping, et al. 2000. Imaging Neuronal Subsets in Transgenic Mice Expressing Multiple Spectral Variants of GFP. *Neuron.* 28:41-51.
Foster, Russel G. 2005. Bright blue times. *Nature.* 433: 698-699.
Gold, Joshua I. et al. 2000. Representation of a perceptual decision in developing oculomotor commands. *Nature.*404: 390-394.
Gordon, Jon W., et al. 1987. Regulation of Thy-1 Gene Expression in Transgenic Mice. *Cell.* 50: 445-452.
Hausser, Michael, et al. 1997. Tonic Synaptic Inhibition Modulates Neuronal Output Pattern and Spatiotemporal Synaptic Integration. *Neuron.* 19: 665-678.
Hirase, Hajime, et al. 2002. Multiphoton stimulation of neurons. *J Neurobiol.* 51(3): 237-47.

(56) References Cited

OTHER PUBLICATIONS

Kandel, E.R., et al. 1961. Electrophysiology of Hippocampal Neurons: I. Sequential Invation and Synaptic Organization. *J Neurophysiol.* 24: 225-242.
Kandel, E.R., et al. 1961. Electrophysiology of Hippocampal Neurons: II. After-Potentials and Repetitive Firing. *J. Neurophysiol.* 24: 243-259.
Katz, Lawrence C. et al. 1994. Scanning laser photostimulation: a new approach for analyzing brain circuits. *J. Neurosci Methods.* 54: 205-218.
Klausberger, Thomas, et al. 2003. Brain-state- and cell-type-specific firing of hippocampal interneurons in vivo. *Nature.* 421: 844-848.
Lima, Susana Q., et al. 2005. Remote Control of Behavior through Genetically Targeted Photostimulation of Neurons. *Cell.* 121: 141-152.
Melyan, Z., et al. 2005. Addition of human melanopsin renders mammalian cells photoresponsive. *Nature.* 433: 741-745.
Mermelstein, Paul G., et al. 2000. Critical Dependence of cAMP Response Element-Binding Protein Phosphorylation on L-Type Calcium Channels Supports a Selective Response to EPSPs in Preference to Action Potentials. *J. Neurosci.* 20(1): 266-273.
Nagel, Georg, et al. 2003. Channelrhodopsin-2, a directly light-gated cation-selective membrane channel. *Proc Nat'l Acad. Sci. USA* 100(24): 13940-13945.
Nirenberg, Sheila, et al. 1997. The Light Response of Retinal Ganglion Cells is Truncated by a Displaced Amacrine Circuit. *Neuron.* 18: 637-650.
Ory, Daniel S., et al. 1996. A stable human-derived packaging cell line for production of high titer retrovirus/vesicular stomatitis virus G pseudotypes. *Proc. Nat'l Acad. Sci. U.S.A.* 93: 11400-11406.
Panda, Satchidananda, et al. 2005. Illumination of the Melanopsin Signaling Pathway. *Science.* 307: 600-604.
Pettit, Diana L., et al. 1999. Local Excitatory Circuits in the Intermediate Gray Layer of the Superior Colliculus. *J. Neurophysiol.* 81(3): 1424-7.
Pouille, Frederic, et al. 2004. Routing of spike series by dynamic circuits in the hippocampus. *Nature.* 429: 717-723.
Qui, Xudong, et al. 2005. Induction of photosensitivity by heterologous expression of melanopsin. *Nature.* 433: 745-749.
Salzman, C. Daniel, et al. 1990. Cortical miucrostimulation influences perceptual judgements of motion direction. *Nature.* 346: 174-177.
Shepherd, Gordon M.G., et al. 2003. Circuit Analysis of Experience-Dependent Plasticity in the Developing Rat Barrel Cortex. *Neuron.* 38: 277-289.
Tatarkiewicz, Krystyna, et al. 1999. Reversal of Hyperglycemia in Mice After Subcutaneous Transplantation of Macroencapsulated Islets. *Transplantation.* 67(5): 665-671.
Yamazoe, Hironori, et al. 2006. Efficient generation of dopaminergic neurons from mouse embryonic stem cells enclosed in hollow fibers. *Biomaterials.* 27: 4871-4880.
Yan, Weiming, et al. 2001. Cloning and Characterization of a Human β,β-Carotene-15, 15'-Dioxygenase That is Highly Expressed in the Retinal Pigment Epithelium. *Genomics.* 72: 193-202.
Yoshimura, Yumiko, et al. 2005. Excitatory cortical neurons form fine-scale functional networks. *Nature.* 433: 868-873.
Zemelman, Boris V., et al. 2002. Selective Photostimulation of Genetically ChARGed Neurons. *Neuron.* 33: 15-22.
Zemelman, Boris V., et al. 2003. Photochemical gating of heterologous ion channels: Remote control over genetically designated populations of neurons. *Proc. Nat'l Acad. Sci. U.S.A.* 100(3): 1352-1357.
1992, Liman, E. R., Tytgat, J., Hess, P., "Subunit Stoichiometry of a Mammalian K+ Channel Determined by Construction of Multimeric cDNAs," Neuron, vol. 9, 861-871, Nov. 1992.
2002, Zrenner, E., "Will Retinal Implants Restore Vision?" Science Feb. 8, 2002, vol. 295, No. 5557, pp. 1022-1025.
1999, Luecke, H., Schobert, B., Richter, H., Cartailler, J., Lanyi, J., "Structural Changes in Bacteriorhodopsin During Ion Transport at 2 Angstrom Resolution," Science Oct. 8, 1999, vol. 286, No. 5438, pp. 255-260.
1992, Takahashi, T., Kubota, M., Watanabe, M., Yoshihara, K., Derguini, F., Nakanishi, K., "Diversion of the Sign of Phototaxis in a Chlamydomonas reinhardtii Mutant Incorporated with Retinal and Its Analogs," FEBS Letters 11878, vol. 314, No. 3, 275-279 (Dec. 1992).
1995, Nagel, G., Mockel, B., Buldt, G., Bamberg, E., "Functional Expression of Bacteriorhodopsin in Oocytes Allows Direct Measurement of Voltage Dependence of Light Induced H+ Pumping," FEBS Letters 16427, vol. 377, 263-266 (1995).
Hildebrandt et al. "Bacteriorhodopsin expressed in *Schizosacch263aromyces pombe* pumps protons through the plasma membrane." PNAS 90, Apr. 1993, pp. 3578-3582.
2007, Feng Zhang et al. "Multimodal fast optical interrogation of neural circuitry." Nature 446: 633-639 (Apr. 2007).
2006, Feng Zhang et al. "Channelrhodopsin-2 and optical control of excitable cells." Nature Methods 3(10): 785-792 (Oct. 2006).
2000, David A. Zacharias et al. "Recent advances in technology for measuring and manipulating cell signals." Current Opinion in Neurobiology 10: 416-421 (2000).
2002, M. Falconer et al. "High-throughput screening for ion channel modulators." J. Biomol. Screen 7: 460-465 (2002) Abstract only.
2003, G. Nagel et al., "Channelrhodophsin-2, a directly light-gated cation-selective membrane channel." PNAS 100: 13940-13945 (Nov. 2003).
2005, Z.-H. Pan et al. "Functional expression of a directly light-gated membrane channel . . . " Invest. Opth. & Visual Science 46 (May 2005). Abstract only.
1997, N. Louis et al. "Cloning and sequencing of the cellular-viral junctions from the human adenovirus type 5 transformed 293 cell line." Virology, 233(2): 423-429 (Jul. 1997). Abstract only.
1996, W. Pear. "Transient Transfection Methods for Preparation of High-Titer Retroviral Supernatants." Supplement 68, Current Protocols in Molecular Biology, 9.11.1-9.11.18, (1996).
1996, R.E. Kingston et al. "Transfection of DNA into Eukarotic Cells." Supplement 63, Current Protocols in Molecular Biology, 9.1.1-9.1.11, John Wiley & Sons, Inc. (1996).
1997, R. Mortensen et al. "Selection of Transfected Mammalian Cells." Supplement 62, Current Protocols in Molecular Biology, 9.5.1-09.5.19, John Wiley & Sons, Inc. (1997).
1996, H. Potter. "Transfection by Electroporation." Supplement 62, Current Protocols in Molecular Biology, 9.3.1-9.3.6, John Wiley & Sons, Inc. (1996).
1997, T. Gulick. "Transfection using DEAE-Dextran." Supplement 40, Current Protocols in Molecular Biology, 9.2.1-9.2.10, John Wiley & Sons, Inc. (1997).
1999, R.E. Kingston et al. "Transfection and Expression of Cloned DNA." Supplement 31, Current Protocols in Immunology (CPI), 10.13.1-10.13.9, John Wiley & Sons, Inc. (1999).
Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.

(56) References Cited

OTHER PUBLICATIONS

Lanyi et al. "The primary structure of a Halorhodopsin from *Natronobacterium Pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers" Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic Systems", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Gold, et al. "Representation of a perceptual decision in developing oculomotor commands", Nature, 2000, vol. 404, pp. 390-394.
Gregory, et al. "Integration site for Streptomyces phage φBT1 and development of site-specific integrating vectors", Journal of Bacteriology, 2003, vol. 185, No. 17, pp. 5320-5323.
Gulick, et al. "Transfection using DEAE-Dextran" Supplement 40, Current Protocols in i0 Molecular Biology, 1997, Supplement 40, 9.2.1-9.2.10.
Hausser, et al. "Tonic Synaptic Inhibition Modulates Neuronal Output Pattern and Spatiotemporal Synaptic Integration", Neuron, 1997, vol. 19, pp. 665-678.
Kingston et al. "Transfection and Expression of Cloned DNA," Supplement 31, Current Protocols in Immunology, 1999, 10.13.1-10.13.9.
Louis et al. "Cloning and sequencing of the cellular-viral junctions from the human adenovirus type 5 transformed 293 cell line," Virology, 1997, vol. 233, pp. 423-429.
Mortensen et al. "Selection of Transfected Mammalian Cells," Supplement 86, Current Protocols in Molecular Biology, 1997, 9.5.1-09.5.19.
Pear "Transient Transfection Methods for Preparation of High-Titer Retroviral Supernatants" Supplement 68, Current Protocols in Molecular Biology, 1996, 9.1 1 .1-9.1 1 .1 8.
Pouille, et al. "Routing of spike series by dynamic circuits in the hippocampus", Nature, 2004, vol. 429: pp. 717-723.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Wells et al. "Application of Infrared light for in vivo neural stimulation," Journal of Biomedical Optics, 2005, vol. 10(6), pp. 064003-1-064003-12.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Xiong et al., "Interregional connectivity to primary motor cortex revealed using MRI resting state images", Hum Brain Mapp, 1999, 8(2-3):151-156.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem,2007,87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila larvae*", Current Biology, Sep. 16, 2006(17):1741-1747.
Tye, et al. "Optogenetic investigation of neural circuits underlying brain disease in animal models," Nature Reviews Neuroscience (Mar. 2012), 13(4):251-266.
Airan, et al., "Temporally Precise in vivo Control of Intracellular Signaling", 2009, Nature, vol. 458, No. 7241, pp. 1025-1029.
Braun, "Two Light-activated Conductances in the Eye of the Green Alga Volvox carteri", 1999, Biophys J., vol. 76, No. 3, pp. 1668-1678.
Cardin, et al. "Driving Fast spiking Cells Induces Gamma Rhythm and Controls Sensory Responses", 2009, Nature, vol. 459, vol. 7247, pp. 663-667.
Deisseroth et al., "Excitation-neurogenesis Coupling in Adult Neural Stem/Progenitor Cells", 2004, Neuron, vol. 42, pp. 535-552.
Ernst, et al. "Photoactivation of Channelrhodopsin", 2008, vol. 283, No. 3, pp. 1637-1643.
Genbank Accession No. DQ094781 (Jan. 15, 2008).
Gradinaru, et al. "ENpHR: a Natronomonas Halorhodopsin Enhanced for Optogenetic Applications", 2008, Brain Cell Biol., vol. 36 (1-4), pp. 129-139.
Herlitze, et al., "New Optical Tools for Controlling Neuronal Activity", 2007, Curr Opin Neurobiol, vol. 17, No. 1, pp. 87-94.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
McAllister, "Cellular and Molecular Mechanisms of Dendrite Growth", 2000, Cereb Cortex, vol. 10, No. 10, pp. 963-973.
Pape, et al., "Plastic Synaptic Networks of the Amygdala for the Acquisition, Expression, and Extinction of Conditioned Fear", 2010, Physiol Rev, vol. 90, pp. 419-463.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.
Sajdyk, et al., "Excitatory Amino Acid Receptors in the Basolateral Amygdala Regulate Anxiety Responses in the Social Interaction Test", Brain Research, 1997, vol. 764, pp. 262-264.

(56) References Cited

OTHER PUBLICATIONS

Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
"SubName: Full=Channelrhodopsin-1", retrieved from EBI accession No. UNIPROT: B4Y103. Database accession No. B4Y103. Sep. 23, 2008.
Balint, et al., "The Nitrate Transporting Photochemical Reaction Cycle of the Pharaonis Halorhodopsin", Biophysical Journal, 2004, vol. 86, pp. 1655-1663.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Gradinaru et al., "Targeting and readout strategies for fast optical neural control in vitro and in vivo", J Neuroscience, 2007, 27(52):14231-14238.
2000, Lee et al. Neurosurgery 46: 1461-1469 (2000).
2000, Berridge et al. Nature Reviews: Molecular Cell Biology 1: 11-21 (2000).
2001, Yan et al. Genomics 72: 193-202 (2001).
1997, Hoffman et al. Nature 387: 869-874 (1997).
1991, Hegemann et al. Biophys. J. 60: 1477-1489 (1991).
2002, Tottene et al. PNAS USA 99: 13284-13289 (2002).
2000, Lim et al. Neuron 25: 385-397 (2000).
1997, Gur et al. Vision Research 37: 377-382 (1997).
Gonzalez, et al., "Cell-Based Assays and Instrumentation for Screening Ion-Channel Targets", DDT, 1999, vol. 4, No. 9, pp. 431439.
Natochin, et al. "Probing rhodopsin-transducin interaction using Drosophila Rh1-bovine rhodopsin chimeras," Vision Res., 2006, vol. 46, No. 27: pp. 4575-4581.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004, pp. 750-769.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.

Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Basil et al. "Is There Evidence for Effectiveness of Transcranial Magnetic Stimulation in the Treatment of Psychiatric Disorders?" Psychiatry, 2005, pp. 64-69.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by $\theta$ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods, 2008, vol. 169, Issue 1. Abstract only.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol., 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

(56) References Cited

OTHER PUBLICATIONS

Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Eisen, "Treatment of amyotrophic lateral sclerosis", Drugs Aging, 1999; vol. 14, No. 3, pp. 173-196.
Evanko "Optical excitation yin and yang" Nature Methods, 2007, 4:384.
Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Foster, "Bright blue times", Nature, 2005, vol. 433, pp. 698-699.
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat", Neuroscience, 1997, vol. 76, No. 3, pp. 689-706.
Gottesman et al."Bacterial regulation: global regulatory networks," Ann. Rev. Genet., 1984, vol. 18, pp. 415-441.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hegemann et al., "All-trans Retinal Constitutes the Functional Chromophore in *Chlamydomonas* rhodopsin", Biophys. J. , 1991, vol. 60, pp. 1477-1489.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 51, No. 3: pp. 237-247.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Johnston et al. "Isolation of the yeast regulatory gene *GAL4* and analysis of its dosage effects on the galactose/melibiose regulon," PNAS, 1982, vol. 79, pp. 6971-6975.
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.

(56) References Cited

OTHER PUBLICATIONS

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khossravani et al., "Voltage-Gated Calcium Channels and Idiopathic Generalized Epilepsies", Physiol. Rev., 2006, vol. 86: pp. 941-966.

Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kingston et al. "Transfection of DNA into Eukaryotic Cells," Supplement 63, Current Protocols in Molecular Biology, 1996, 9.1.1-9.1.11, 11 pages.

Kita, H. et al. "Effects of dopamine agonists and antagonists on optical responses evoked in rat frontal cortex slices after stimulation of the subcortical white matter," Exp. Brain Research, 1999, vol. 125, pp. 383-388.

Kitayama, et al. "Regulation of neuronal differentiation by $N$-methyl-D-aspartate receptors expressed in neural progenitor cells isolated from adult mouse hippocampus," Journal of Neurosci Research, 2004, vol. 76, No. 5: pp. 599-612.

Klausberger, et al. "Brain-state- and cell-type-specific firing of hippocampal interneurons in vivo", Nature, 2003, vol. 421: pp. 844-848.

Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.

Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

Landy, A. "Mechanistic and structural complexity in the site-specific recombination pathways of Int and FLP", Current Opinion in Genetics and Development, 1993, vol. 3, pp. 699-707.

Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

Levitan et al. "Surface Expression of Kv1 Voltage-Gated K+ Channels Is Governed by a C-terminal Motif," Trends Cardiovasc. Med., 2000, vol. 10, No. 7, pp. 317-320.

Li et al. "Fast noninvasive activation and inhibition of neural and network activity by vertebrate rhodopsin and green algae channelrhodopsin." PNAS, 2005, vol. 102, No. 49, p. 17816-17821.

Lim et al., "A Novel Targeting Signal for Proximal Clustering of the Kv2.1K+ Channel in Hippocampal Neurons", Neuron, 2000, vol. 25: pp. 385-397.

Lima, et al. "Remote Control of Behavior through Genetically Targeted Photostimulation of Neurons", Cell, 2005, vol. 121: pp. 141-152.

Liman, et al. "Subunit Stoichiometry of a Mammalian K+ Channel Determined by Construction of Multimeric cDNAs," Neuron, 1992, vol. 9, pp. 861-871.

Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of *FRT* sites in the maize genome," Nucleic Acids Research, 1996, vol. 24, No. 19: pp. 3784-3789.

Ma et al. "Role of ER Export Signals in Controlling Surface Potassium Channel Numbers," Science, 2001, vol. 291, pp. 316-319.

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

McKnight "Functional relationships between transcriptional control signals of the thymidine kinase gene of herpes simplex virus", Cell, 1982, vol. 31 pp. 355-365.

Melyan, Z., et al. "Addition of human melanopsin renders mammalian cells Photoresponsive", Nature, 2005, vol. 433: pp. 741-745.

Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.

Monje et al., "Irradiation Induces Neural Precursor-Cell Dysfunction", Natural Medicine, 2002, vol. 8, No. 9, pp. 955-962.

Nacher, et al. "NMDA receptor antagonist treatment increases the production of newneurons in the aged rat hippocampus", Neurobiology of Aging, 2003, vol. 24, No. 2: pp. 273-284.

Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.

Nagel, et al. "Channelrhodopsin-I: a light-gated proton channel in green algae", Science, 2002, vol. 296: pp. 2395-2398.

Nakagami, et al. "Optical Recording of Trisynaptic Pathway in Rat Hippocampal Slices with a Voltage-Sensitive Dye" Neuroscience, 1997, vol. 81, No. 1, pp. 1-8.

Nirenberg, et al. "The Light Response of Retinal Ganglion Cells is Truncated by a Displaced Amacrine Circuit", Neuron, 1997, vol. 18: pp. 637-650.

Nunes-Duby, et al. "Similarities and differences among 105 members of the Int family of site-specific recombinases", Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.

Ory, et al. "A stable human-derived packaging cell line for production of high titer retrovirus/vesicular stomatitis virus G pseudotypes," PNAS, 1996, vol. 93: pp. 11400-11406.

Palmer et al., "The Adult Rat Hippocampus Contains Primordial Neural Stem Cells", Molecular and Cellular Neuroscience, 1997, vol. 8, pp. 389-404.

Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.

Panda, et al. "Illumination of the Melanopsin Signaling Pathway", Science, 2005, vol. 307: pp. 600-604.

Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.

Pear "Transient Transfection Methods for Preparation of High-Titer Retroviral Supernatants" Supplement 68, Current Protocols in Molecular Biology, 1996, 9.1 1 .I -9.1 1 .I 8.

Petersen et al. "Spatiotemporal Dynamics of Sensory Responses in Layer ⅔ of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.

Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.

Pettit, et al. "Local Excitatory Circuits in the Intermediate Gray Layer of the Superior Colliculus", J Neurophysiol., 1999, vol. 81, No. 3: pp. 1424-1427.

Potter, "Transfection by Electroporation." Supplement 62, Current Protocols in Molecular Biology, 1996, 9.3.1-9.3.6.

Qiu et al. "Induction of photosensitivity by heterologous expression of melanopsin", Nature, 2005, vol. 433: pp. 745-749.

Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.

(56) References Cited

OTHER PUBLICATIONS

Rosenkranz, et al. "The prefrontal cortex regulates lateral amygdala neuronal plasticity and responses to previously conditioned stimuli", J. Neurosci., 2003, vol. 23, No. 35: pp. 11054-11064.

Rubinson et at. "A lentivirus-based system to functionally silence genes in primary mammalian cells, stem cells and transgenic mice by RNA interference," Nature Genetics, 2003, vol. 33, p. 401-406.

Rudiger et at. "Specific arginine and threonine residues control anion binding and transport in the light-driven chloride pump halorhodopsin," The EMBO Journal, 1997, vol. 16, No. 13, pp. 3813-3821.

Salzman, et al. "Cortical microstimulation influences perceptual judgements of motion direction", Nature, 1990, vol. 346, pp. 174-177.

Sato et al. "Role of Anion-binding Sites in cytoplasmic and extracellular channels of *Natronomonas pharaonis* halorhodopsin," Biochemistry, 2005. vol. 44, pp. 4775-4784.

Sauer "Site-specific recombination: developments and applications," Current Opinion in Biotechnology, 1994, vol. 5, No. 5: pp. 521-527.

Sclimenti, et al. "Directed evolution of a recombinase for improved genomic integration at a native human sequence," Nucleic Acids Research, 2001, vol. 29, No. 24: pp. 5044-5051.

Shepherd, et al. "Circuit Analysis of Experience-Dependent Plasticity in the Developing Rat Barrel Cortex", Neuron, 2003, vol. 38: pp. 277-289.

Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.

Silver, et al. "Amino terminus of the yeast *GAL4* gene product is sufficient for nuclear localization" PNAS, 1984, vol. 81, No. 19: pp. 5951-5955.

Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.

Smith et al. "Diversity in the serine recombinases", Molecular Microbiology, 2002, vol. 44, No. 2: pp. 299-307.

Stark, et al. "Catalysis by site-specific recombinases," Trends Genet., 1992, vol. 8, No. 12: pp. 432-439.

Stockklausner et al. "A sequence motif responsible for ER export and surface expression of Kir2.0 inward rectifier K+ channels," FEBS Letters, 2001, vol. 493, pp. 129-133.

Stoll, et al. "Phage TP901-I site-specific integrase functions in human cells," Journal of Bacteriology, 2002, vol. 184, No. 13: pp. 3657-3663.

Takahashi, et al. "Diversion of the Sign of Phototaxis in a *Chlamydomonas reinhardtii* Mutant Incorporated with Retinal and Its Analogs," FEBS Letters, 1992, vol. 314, No. 3, pp. 275-279.

Tatarkiewicz, et al. "Reversal of Hyperglycemia in Mice After Subcutaneous Transplantation of Macroencapsulated Islets", Transplantation, 1999, vol. 67, No. 5: pp. 665-671.

Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.

Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.

[No Authors Listed] "Two bright new faces in gene therapy," Nature Biotechnology, 1996, vol. 14: p. 556.

Tye et. al., "Amygdala circuitry mediating reversible and bidirectional control of anxiety", Nature, 2011, vol. 471(7338): pp. 358-362.

Tye et. al., Supplementary Materials: "An optically-resolved microcircuit for bidirectional anxiety control", Nature, 2011, vol. 471(7338): pp. 358-362.

Ulmanen, et al. "Transcription and translation of foreign genes in *Bacillus subtilis* by the aid of a secretion vector," Journal of Bacteriology, 1985, vol. 162, No. 1: pp. 176-182.

Wagner, "Noninvasive Human Brain Stimulation", Annual Rev. Biomed. Eng. 2007. 9:19.1-19.39.

Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.

Wang et al. "Direct-current Nanogenerator Driven by Ultrasonic Waves," Science, 2007, vol. 316, pp. 102-105.

Wang et. al., "High-speed mapping of synaptic connectivity using photostimulation in Channelrhodopsin-2 transgenic mice", PNAS, 2007, vol. 104, No. 19, pp. 8143-8148.

Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.

Witten et. al., Supporting Online Material for: "Cholinergic Interneurons Control Local Circuit Activity and Cocaine Conditioning", Science, 2010, vol. 330: 17 pages.

Witten et. al., "Cholinergic Interneurons Control Local Circuit Activity and Cocaine Conditioning", Science, 2010, vol. 330, No. 6011: pp. 1677-1681.

Yamazoe, et al. "Efficient generation of dopaminergic neurons from mouse embryonic stem cells enclosed in hollow fibers", Biomaterials, 2006, vol. 27, pp. 4871-4880.

Yizhar et. al., "Neocortical excitation/inhibition balance in information processing and social dysfunction", Nature, 2011, vol. 477, pp. 171-178; and Supplemental Materials; 41 pages.

Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.

Zemelman, et al. "Selective Photostimulation of Genetically ChARGed Neurons", Neuron, 2002, vol. 33: pp. 15-22.

Zemelman, et al. "Photochemical gating of heterologous ion channels: Remote control over genetically designated populations of neurons", PNAS, 2003, vol. 100, No. 3: pp. 1352-1357.

Zhang, et al. "Red-Shifted Optogenetic Excitation: a Tool for Fast Neural Control Derived from Volvox carteri", Nature Neurosciences, 2008, vol. 11, No. 6, pp. 631-633.

Zrenner, E., "Will Retinal Implants Restore Vision?" Science, 2002, vol. 295, No. 5557, pp. 1022-1025.

Zufferey, et al. "Self-Inactivating Lentivirus Vector for Safe and Efficient in Vivo Gene Delivery", Journal of Virology, 1998, vol. 72, No. 12, pp. 9873-9880.

Cazillis et al., "VIP and PACAP induce selective neuronal differentiation of mouse embryonic stem cells", Eur J Neurosci, 2004, 19(4):798-808.

Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.

Arenkiel, et al. "In vivo light-induced activation of neural circuitry in transgenic mice expressing Channelrhodopsin-2", Neuron, 2007, 54:205-218.

Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

Bebbington et al., The use of vectors based on gene amplification for the expression of cloned genes in mammalian cells in "DNA cloning" vol. 3, Academic Press, New York, 1987.

Peterlin, et al. "Optical probing of neuronal circuits with calcium indicators," PNAS, 2000, vol. 97, No. 7: pp. 3619-3624.

(56) References Cited

OTHER PUBLICATIONS

Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
U.S. Appl. No. 13/299,727, filed Nov. 18, 2011, Lee, et al.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Li et al., "Surface Expression of Kv1 Channels is Governed by a C-Terminal Motif", J. Bioi. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.

Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496(7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491(7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9(4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8(8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

(56) References Cited

OTHER PUBLICATIONS

Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse *Ren-2* gene", Nature, 1990, vol. 344, pp. 541-544.
Mullins et al., "Expression of the DBA/2J *Ren-2* gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (May 9, 2012).
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full=Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

Mueller, et al.; "Clinical Gene Therapy Using Recombinant Adeno-Associated Virus Vectors"; Gene Therapy; vol. 15, pp. 858-863 (2008).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Han, et al., "Millisecond-Timescale Optical Control of Neural Dynamics in the Nonhuman Primate Brain"; Neuron; vol. 62, pp. 191-198 (Apr. 30, 2009).
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900 (Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl. 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct 2003).
Samuelson; "Post-traumatic stress disorder and declarative memory functioning: a review"; Dialogues in Clinical Neuroscience; vol. 13, No. 3, pp. 346-351 (2011).

\* cited by examiner

SCREENING TEST DRUGS TO IDENTIFY THEIR EFFECTS ON CELL MEMBRANE VOLTAGE-GATED ION CHANNEL

RELATED PATENT DOCUMENTS

This patent document claims the benefit, under 35 U.S.C. §119(e), of U.S. Provisional Patent Application Ser. No. 60/955,116, entitled Cell Line, System and Method for Optical-Based Screening of Ion-Channel Modulators and filed on Aug. 10, 2007; this patent document is fully incorporated herein by reference.

This patent document also claims priority, as a CIP under 35 U.S.C. §120, to the following patent documents which are also individually incorporated by reference: U.S. patent application Ser. No. 11/651,422 filed on Jan. 9, 2007 now U.S. Pat. No. 8,926,959 and entitled, System for Optical Stimulation of Target Cells), which is a CIP of U.S. patent application Ser. No. 11/459,636 filed on Jul. 24, 2006 now U.S. Pat. No. 8,906,360 and entitled, Light-Activated Cation Channel and Uses Thereof, which claims the benefit of U.S. Provisional Application No. 60/701,799 filed Jul. 22, 2005.

FEDERALLY-SPONSORED RESEARCH OR DEVELOPMENT

This invention was made with Government support under contract OD000616 awarded by the National Institutes of Health. The Government has certain rights in this invention.

FIELD OF THE INVENTION

The present invention relates generally to systems and approaches for screening drug candidates and more particularly to a cell line, system and method for optically-based screening of the drug candidates with respect to their effect on cellular ion channels.

BACKGROUND

Ion channels and ion pumps are cell-membrane proteins that control the transport of positively or negatively charged ions (e.g., sodium, potassium and chloride) across the cell membrane. Ion channels play an important part of various animal and human functions including signaling and metabolism. Ion-channel dysfunctions are associated with a wide variety of illnesses. For instance, diseases resulting from ion-channel dysfunctions in the central nervous system include anxiety, depression, epilepsy, insomnia, memory problems and chronic pain. Other diseases resulting from ion-channel dysfunctions include cardiac arrhythmia, and type II diabetes. Researchers are continually discovering diseases associated with ion-channel functionality.

Several drugs have been discovered to modify ion-channel functionality; however, the number of clinically approved drugs for restoring ion-channel functionality is limited. A major bottleneck in the discovery and development of new ion-channel drugs lies in the technical challenge of quickly, efficiently and cheaply screening drug candidates to identify structures that affect ion-channel functionality. Common screening techniques use patch clamping to measure the voltage and/or current in a cell. Micropipettes affixed to the cell membrane obtain the measurement. For example, whole-cell configuration can be used to monitor the functionality of the ion channels throughout the cell. In this manner, changes in voltage or current due to an introduced drug can be monitored. Such methods require contact between the micropipette and the cell. For this and other reasons, such techniques leave room for improvement in their ability to screen drugs quickly, efficiently and cheaply.

These and other issues have presented challenges to screening of drug candidates, including those affecting ion-channel function.

BRIEF DESCRIPTION OF THE DRAWINGS

The invention may be more completely understood in consideration of the detailed description of various embodiments of the invention that follows in connection with the accompanying drawings, in which.

Figure 1A:
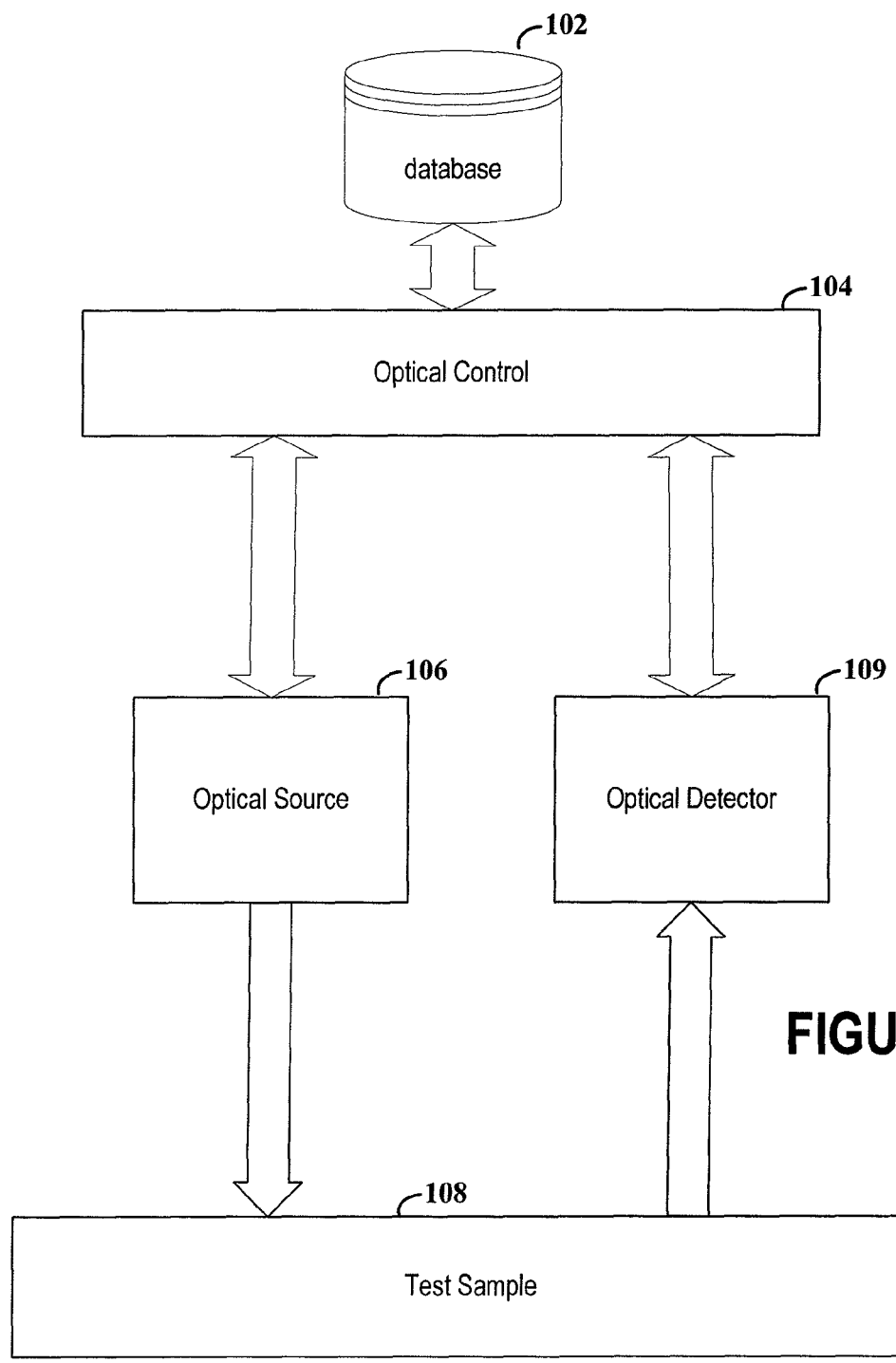
FIG. 1A shows a block diagram of a system for optical drug screening, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of optical-based screening systems, and the invention has been found to be particularly suited for use in systems and methods dealing with identification of ion-channel modulating drugs. While the present invention is not necessarily limited to such applications, various aspects of the invention may be appreciated through a discussion of various examples using this context.

Recently discovered techniques allow for stimulation of cells resulting in the rapid depolarization of cells (e.g., in the millisecond range). Such techniques can be used to control the depolarization of cells such as neurons. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different biological applications, among others including psychological therapy, muscle control and sensory functions. For further details on specific implementations of photosensitive bio-molecular structures and methods, reference can be made to one or more of the above-listed patent documents (by Karl Deisseroth et al.) which are fully incorporated herein by reference. These references discuss use of blue-light-activated ion-channel channelrhodopsin-2 (ChR2) to cause calcium (Ca++)-mediated neural depolarization. Also discussed in one or more of these references are other applicable light-activated ion channels including, for example, halorhodopsin (NpHR) in which amber light affects chloride (Cl−) ion flow so as to hyperpolarize neuronal membrane, and make it resistant to firing. Collectively, these light-sensitive proteins, serving to regulate membrane voltage using ion switches that, when activated (or deactivated) in response to light, function as channels or pumps, are referred to herein as light-responsive ion switches or light-activated membrane potential switches (LAMPS).

Consistent with one example embodiment of the present invention, a system screens for ion-channel and ion-pump affecting compounds. The system introduces one or more drug candidates that could either block or enhance the activity of ion-channels or ion-pumps to cells that were made optically responsive by the addition of the above mentioned proteins (ChR2 and NpHR), for the purpose of screening the drug candidates. Light triggers optically responsive ion channels in the cells causing a change in the voltage seen across the cell membrane. The voltage change stimulates voltage-gated ion channels in the cells which will then cause a change in ion concentrations that can be read as optical outputs. These optical signals are detected and used to determine what effect, if any, the drug candidates have on the voltage-gated ion channels.

In addition to NpHR and ChR2, there are a number of channelrhodopsins, halorhodopsins, and microbial opsins that can be engineered to optically regulate ion flux or second messengers within cells. Various embodiments of the invention include codon-optimized, mutated, truncated, fusion proteins, targeted versions, or otherwise modified versions of such ion optical regulators. Thus, ChR2 and NpHR (e.g., GenBank accession number is EF474018 for the 'mammalianized' NpHR sequence and EF474017 for the 'mammalianized' ChR2(1-315) sequence) are used as representative of a number of different embodiments. Discussions specifically identifying ChR2 and NpHR are not meant to limit the invention to such specific examples of optical regulators. For further details regarding the above mentioned sequences reference can be made to "Multimodal fast optical interrogation of neural circuitry" by Feng Zhang, et al, Nature (Apr. 5, 2007) Vol. 446: 633-639, which is fully incorporated herein by reference.

In one instance, the system allows for different drug candidates to be screened without necessitating extensive setup between screenings. For example, an assay may be performed using optics both to stimulate the optically responsive cells and to detect the effectiveness of the drug. The use of optics instead of manual contacts, e.g., using a whole-cell patch clamp, can be particularly useful in increasing the throughput of the assay screening process. For instance, the time between screenings can be reduced by minimizing or eliminating physical manipulations otherwise necessary to stimulate or detect ion flow in the target cells. The cells can also be prepared prior to the screening process because the test equipment need only be optically coupled to the prepared cells. In another instance, throughput may be increased by screening a number of different drugs simultaneously using, for example, an array of photo detectors and a corresponding array of modified cells exposed to different drugs.

Consistent with another embodiment of the present invention, an optically-responsive cell line is created to screen for drugs that affect the functionality of ion channels. The cell line includes cells that co-express optically responsive ion switches of Channelrhodopsin-2 (ChR2) or NpHR, a voltage-gated Ca2+ channel and a hyperpolarizing channel/pump (e.g., hERG or TASK1, that can lower the membrane voltage to a point where the voltage-gated Ca2+ channel will be in a closed state). The system measures the concentration of Ca2+ using an indicator dye (e.g., Fura-2) or genetically encoded activity sensor. The above mentioned components are introduced to the cell line by standard liposomal transfection methods and the ChR2 related channel is stimulated using (blue) light; for further information in the regard, reference may be made to the patent documents cited herein and to the articles cited supra. Time lapse images of light from the Ca2+ sensitive portion of the system are taken and stored as data. A processor analyzes the data to identify potential channel-affecting drugs. For instance, the processor may identify all chemicals that have concentrations of Ca2+ that do not fall within expected parameters (e.g., concentrations that exceed or are less than an expected range of concentrations).

In a specific instance, the cell line is derived from 293T cells by co-expressing ChR2 and a voltage-gated Ca2+ channel. The 293T cells (and 293T cell line) are a variant of Human Embryonic Kidney (HEK) cells that include the Simian vacuolating virus 40 (SV40) T antigen (see, e.g., N. Louis, C. Evelegh F. L. Graham, *Cloning and sequencing of the cellular-viral junctions from the human adenovirus type 5 transformed* 293 *cell line, Virology,* 233(2):423-9, Jul. 7, 1997; see also U.S. Pat. No. 5,939,320 to Littman, et al. filed Jun. 19, 1996, U.S. Pat. No. 6,790,657 to Arya filed Jun. 28, 2001 and U.S. Pat. No. 6,489,115 to Lahue, et al. filed Dec. 3, 2002). Expression of the light-responsive ion channels, the voltage-gated ion channels and the hyperpolarizing channels by the 293T cells may be accomplished using appropriate transfection vectors.

More specifically, the cell lines may be derived from a stable homogeneous cell line such as HEK293, NIH3T3, or CHO. Several genes responsible for making different subunits of calcium channels have been introduced into the cell lines to provide functional calcium channel activity. In addition to the calcium channel genes, an inward-rectifying potassium channel may be expressed to mimic the natural state of calcium channels by maintaining a more hyperpolarized membrane potential (compared to the default resting membrane potential of HEK293, NIH3T3, or CHO cell lines). Also, a light-activated cation channel channelrhodopsin-2 (ChR2) may be expressed to facilitate optical depolarization and subsequent activation of the calcium channels. Another option includes the expression of a light-activated chloride pump Natronomonas pharonis halorhodopsin (NpHR) to enable rapid optical hyperpolarization of the cell membrane potential.

This cell line based approach is not limited to voltage-gated calcium channels. For example, similar cell lines can be created for voltage-gated sodium (e.g., $Na_v1.1$ through $Na_v1.9$), potassium (e.g., $K_v$ such as hERG, TASK1, Shaker, or KvLQT1), or chloride conducting channels/pumps (e.g., members of the CLC family of chloride channels). The methods of introducing such genes into the cell line are known in the art and may include, for example liposomal tranfection, or viral gene transfer. For further information in this regard, reference may be made to one or more of the following references:

Warren Pear, Transient Transfection *Methods for Preparation of High-Titer Retroviral Supernatants*, Supplement 68, Current Protocols in Molecular Biology, 9.11.1-9.11.18, John Wiley & Sons, Inc. (1996).

R. E. Kingston C. A. Chen, H. Okayama, and J. K. Rose, *Transfection of DNA into Eukarotic Cells*. Supplement 63, Current Protocols in Molecular Biology, 9.1.1-9.1.11, John Wiley & Sons, Inc. (1996).

R. Mortensen, J. D. Chesnut, J. P. Hoeffler, and R. E. Kingston, *Selection of Transfected Mammalian Cells*, Supplement 62, Current Protocols in Molecular Biology, 9.5.1-09.5.19, John Wiley & Sons, Inc. (1997).

H. Potter, *Transfection by Electroporation*, Supplement 62, Current Protocols in Molecular Biology, 9.3.1-9.3.6, John Wiley & Sons, Inc. (1996).

T. Gulick, *Transfection using DEAE-Dextran*, Supplement 40, Current Protocols in Molecular Biology, 9.2.1-9.2.10, John Wiley & Sons, Inc. (1997).

R. E. Kingston, C. A. Chen, H. Okayama, *Transfection and Expression of Cloned DNA*, Supplement 31, Current Protocols in Immunology (CPI), 10.13.1-10.13.9, John Wiley & Sons, Inc.

Each of the above references is incorporated by reference.

These and other transfer vectors may be generated using various genetic engineering techniques. For instance, the transfer vectors may be derived from a provirus clone of a retrovirus, such as an immunodeficiency virus (e.g., HIV-1 or HIV-2, or SIV). For further details on the use of 293T cells and transfection thereof, reference can be made to U.S. Pat. No. 6,790,657 (entitled, Lentivirus Vector System, to Arya), which is fully incorporated herein by reference.

In one embodiment of the invention, optical stimulation of the modified cells may be altered to determine specific properties of an introduced drug candidate. For example, the intensity of the optical stimulus may be modified to change the corresponding level of depolarization. The level of desired depolarization can be tuned to further characterize the effectiveness of the drug under test. In another example, the optical stimulus may include rapid pulsing of the light. By correlating the temporal relationship between the optical stimulus and the resultant detected fluorescence, the drug may be further characterized in terms of a kinetic response. Thus, the drug may be characterized for a variety of different aspects including, but not limited to, the steady state effect on ion concentrations, a change in the level of depolarization necessary to trigger the voltage gated ion channels and the effect on repeated depolarization.

In one embodiment, the system allows for simple calibration of the optical stimulation and/or detection. The modified cells may be optically stimulated prior to introduction of the drug candidate. The ion channel responsiveness is detected and recorded. The recorded values may be used as a baseline for comparison to the ion channel responsiveness of the same modified cells after the introduction of the drug under test. The recorded values may also be used to modify the optical stimulus or the sensitivity of the optical detector. Such modifications may be applied to an individual test sample or an array of test samples. For such an array of test samples, each test sample may be individually calibrated by adjusting the corresponding optical stimulus. Similarly, each corresponding photo detector may be individually adjusted.

FIG. 1A shows a basic block diagram of a system for screening for ion-channel affecting drugs, according to an embodiment of the invention. Optical control 104 communicates with database 102, optical source 106 and optical detector 109. Optical source 106 provides optical stimulus to test sample 108. Test sample 108 includes the drug under test, cells with optically responsive ion channels, and a voltage/ion indicator. In one instance, the indicator fluoresces in response to light from optical source 106. Optical control 104 may also include a reconfigurable readout, so that as different LAMPS and different LEIAs are used, the same control system can be readily adapted to each paradigm. Optical detector 109 produces a signal responsive to such florescence, and optical control 104 receives the produced signal. The optical control 104 stores data obtained from the signal in database 102. The information stored may include factors such as the intensity, duration and wavelength of the detected light. In a particular instance, the stored data can be compared against baseline data, where the baseline data corresponds to data recorded prior to the introduction of the drug to the test sample 108. In another instance, optical source 106 may vary the intensity, duration or other parameters related to the control of optical source 106. These and other parameters may be stored in database 102.

It should be apparent that optical source 106 may be implemented using a single light source, such as a light-emitting diode (LED), or using several light sources. Similarly, optical detector 109 may use one or more detectors and database 102 may be implemented using any number of suitable storage devices.

Figure 1B:
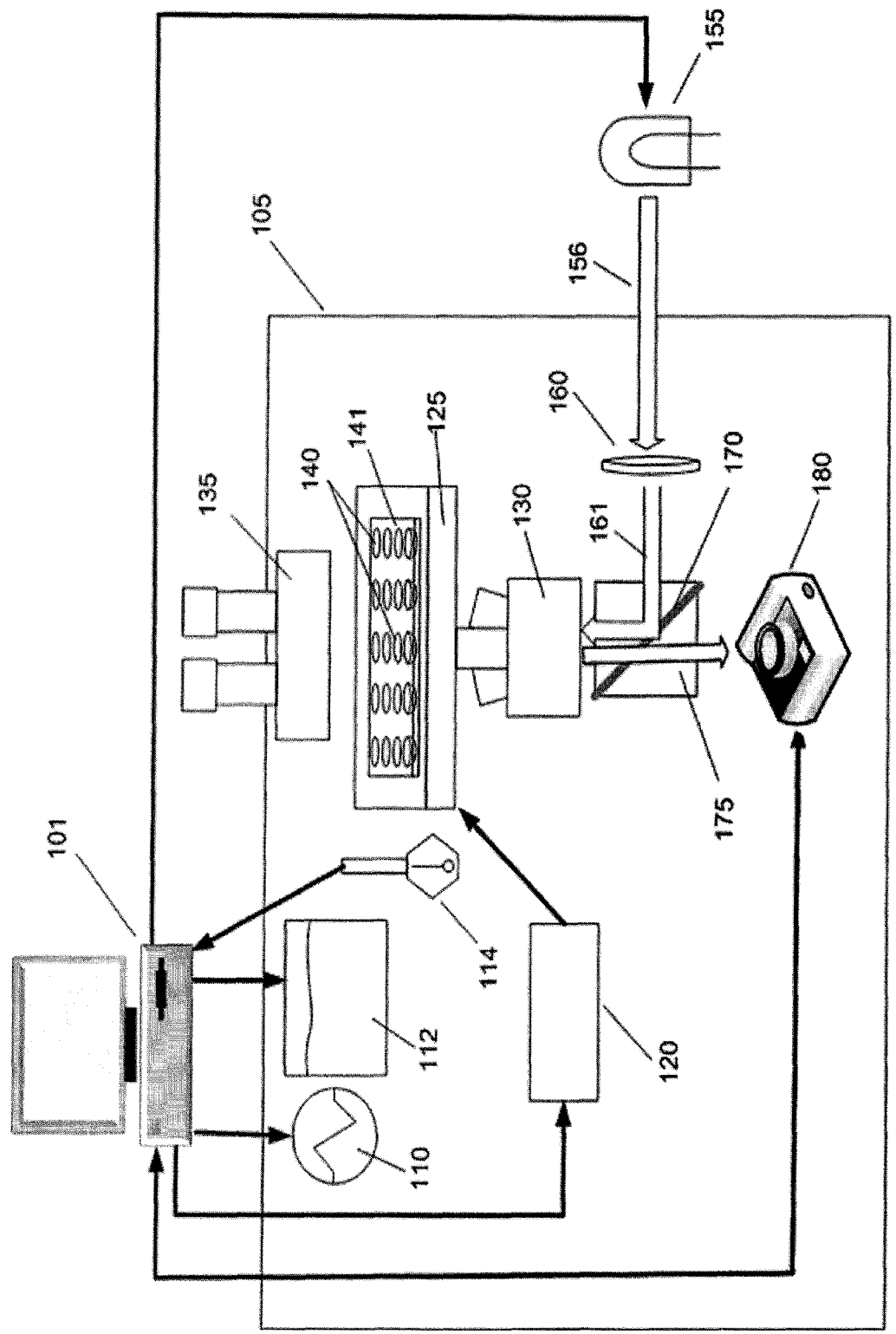
FIG. 1B shows a specific system diagram of a large-format, quasi-automated system for drug screening in accordance with the present methodology, according to an example embodiment of the present invention.

FIG. 1B shows a system diagram of a large-format, quasi-automated system for drug screening in accordance with a specific embodiment of the invention. Control device 101 (e.g., a computer or control logic) controls various processes, and serves as the central point of system input/output functions. The environment may be maintained at an appropriate temperature, humidity, carbon dioxide level and ambient light level within the walls of the climate control chamber 105, with the help of one or more sensors 114 (e.g., thermostat, carbon dioxide sensor and humidity sensor), carbon dioxide and humidifier apparatus 112, and heater 110. Multi-well tray 141 contains test wells 140 for holding cultured cells, drugs, and other ingredients needed for each test. Tray 141 rests upon X-Y-Z table 125, the movement of which is carried out by table actuators 120, under control of computer 101. Xenon lamp 155 emits high-intensity white light 156, which is passed through color filter 160. In the case that ChR2 is used for stimulating the cells within wells 140, color filter 160 is blue, causing blue light 161 to exit the filter, and strike dichroic mirror 170. Blue light 161 then passes upward, through microscope objective lens apparatus 130, and through bottom of transparent tray 141. In this fashion, the contents of wells 140, with their transparent undersides, are illuminated. When a separate wavelength of light is required to stimulate a fluorescent light-emitting indicator of cellular activity, a filter of the appropriate specification may be substituted for the previous filter 160, causing light of the proper wavelength for this latter task to be piped toward well 140. If the cells within well 140 have been light-sensitized, and if the drug being tested in each of these wells does not suppress the process, a light-emitting indicator of cellular activity (LEIA), which has also been added to each well or expressed by the cells via genetic modification, will emit light in accordance with the voltage change caused by the effect of the light. This second wavelength of light, which may be much smaller in magnitude than the stimulation light, is collected by microscope turret 135, and will also be passed through dichroic mirror 175, onto the lens of (CCD) camera 180.

Dichroic mirror 170 allows for upward reflection of both the wavelength required to stimulate the optical gating of the membrane (e.g., blue for ChR2), and the wavelength required by any LEIA used (e.g., ultraviolet for FURA-2). This dichroic mirror may be arranged to allow passage of the output spectrum of the LEIA (e.g., blue-green for FURA-2) with minimal reflection or absorption.

Figure 2:
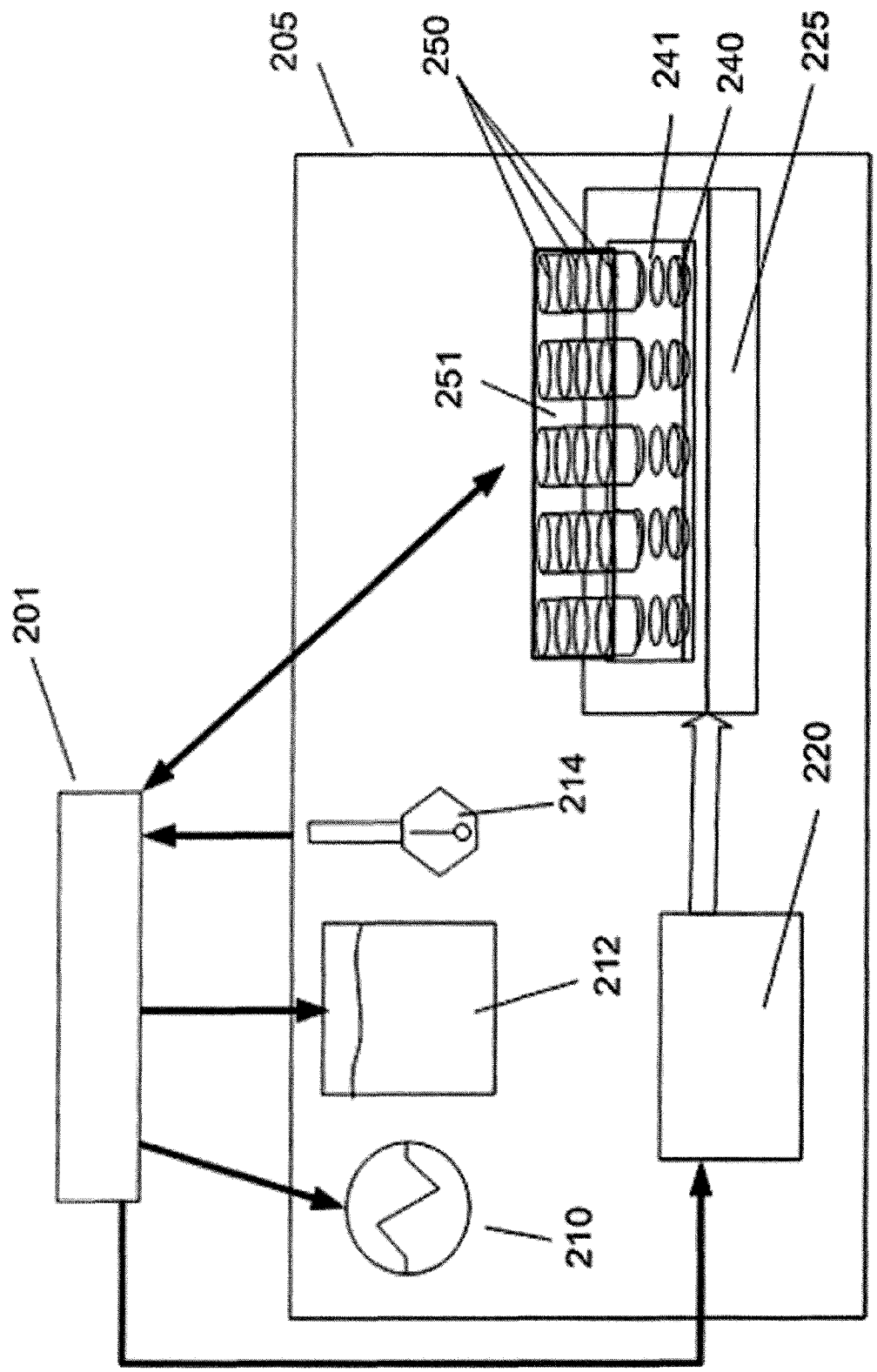
FIG. 2 shows a system diagram of a small-format, fully automated drug screening system which operates in accordance with the invented methodology, according to an example embodiment of the present invention.

FIG. 2 is a system diagram of an automated-drug-screening system, according to an example embodiment of the invention. Emitter/detector units 250 make up the emitter/detector array 251. Emitter/detector array 251 matches the number, size, and layout of the wells on tray 240. Tray holding device 225 permits tray swapping mechanism 220 to rapidly move a new tray into position once testing of a given tray has been completed. The entire process may be automated, and under the control of device 201. Device 201 can be implemented using a computer, control logic, programmable logic arrays, discrete logic and the like. The introduction of the drug candidates under test can also be automated using a machine that provides a reservoir for storing the drugs and a dispensing nozzle for injecting the drugs into the tray. In a manner similar to that shown by FIG. 1, the environment within the walls of the climate control chamber 205 may be maintained at an appropriate temperature, humidity, carbon dioxide level and ambient light level, with the help of thermostat, carbon dioxide sensor and humidity sensor 214, carbon dioxide and humidifier apparatus 212, and heater 210. The use of multiple stimulator/detector elements simultaneously and in parallel, can be particularly useful for augmenting the speed of the overall process. Low cost elements may be used to make multiple parallel detectors (e.g., the components detailed below in description of FIGS. 3A and 3B), the multiple parallel emitter/detector units may also be quite economically feasible.

Figure 3A:
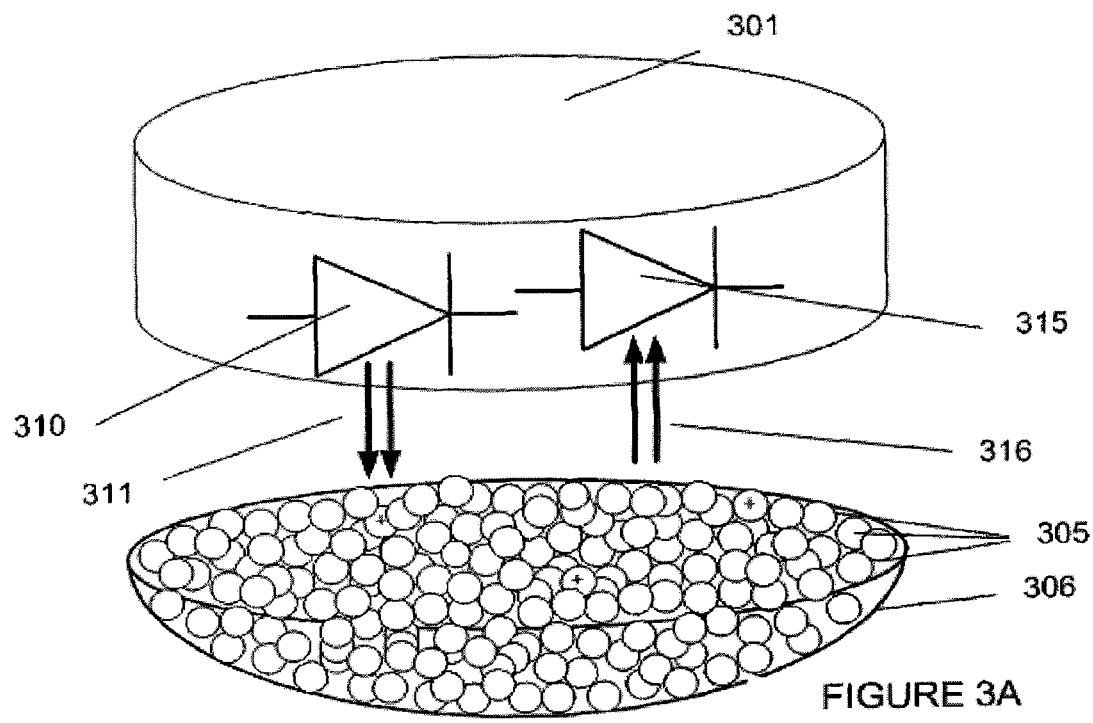
FIG. 3A depicts the workings of an example of emitter/detector units, according to an example embodiment of the present invention.

FIG. 3A depicts the workings of emitter/detector units, such as those shown in FIG. 2, according to an example embodiment of the invention. An LED stimulates light-sensitive ion channels of cells located within a well, and a photodiode detects the response of a LEIA. In this embodiment, device 301 includes LED 310, which produces light pulses 311, at the proper wavelength, pulse frequency and intensity, so as to stimulate light-sensitive transgenic cells 305 in culture within well 306. In the case that ChR2 is the molecular target being used, blue light of 1-10 mW/mm2 is generally appropriate. Due to the presences of an LEIA (e.g., a voltage-sensitive dye or a calcium dye), light 316 is returned from cells 305, and is detected by photodiode 315. In the case that RH 1691 being used, red light is fluoresced and detected by photodiode 315. In the absence of cellular depolarization, no fluorescence is detected by photodiode 315. Other light detecting technologies may also be used instead of a photodiode including phototransistors, and CCD elements.

The combination of photostimulation with optical imaging techniques of LEIAs may be useful for a number of different reasons. For example, photostimulation may simplify the study of excitable cells by reducing the need to use mechanical electrodes for stimulation. Several commercially available LEIAs are suitable for photogrammetrically indicating the activation of electrically excitable cells. One such LEIA is calcium dye Fura-2, which may be stimulated with violet/ultraviolet light around 340 nm, and whose fluorescent output is detectable as blue-green light around 535 nm. Another example is voltage sensitive dye RH 1691, which may be stimulated with green light at about 550 nm, and whose fluorescent output is detectable as red light at about 70 nm. Another example is voltage sensitive dye di-4-ANEPPS, which is stimulated by blue light at about 560 nm, and whose fluorescent output is detectable as red light at about 640 nm.

Figure 3B:
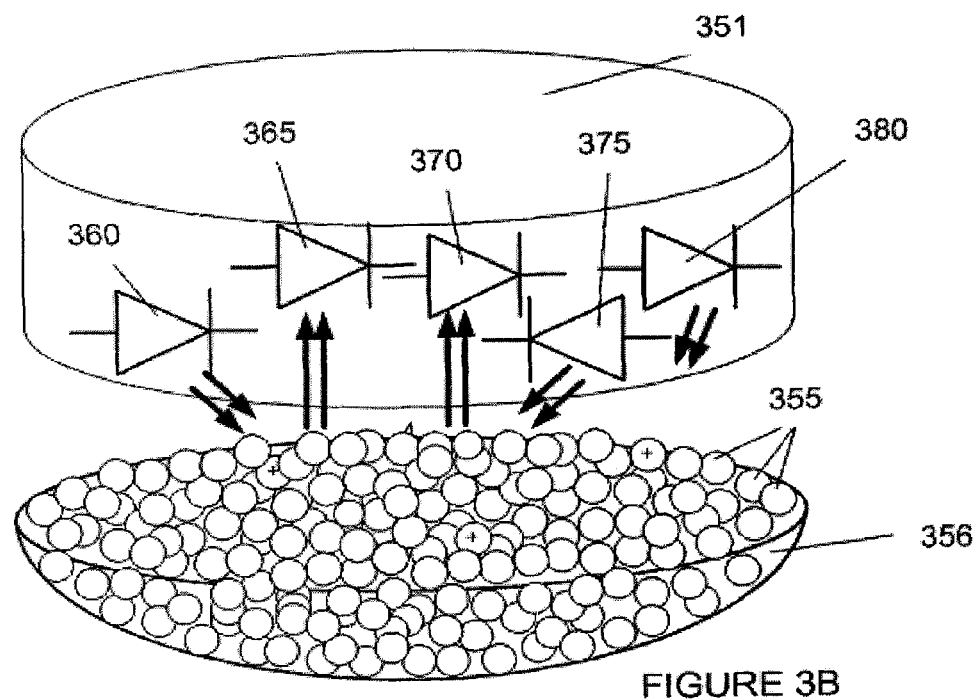
FIG. 3B depicts the workings of another embodiment of emitter/detector units, according to an example embodiment of the present invention.

FIG. 3B depicts the workings of another embodiment of the emitter/detector units shown in the FIG. 2, in which multiple effects are tested within the context of a single well. For example, the cells 355 in the wells 356 may express both ChR2 and NpHR, and hence be sensitive to both the depolarizing effects of blue light, and the hyperpolarizing effects of amber light. Device 351 includes LED 360, which is used for the stimulation of the targeted ion channel or pump (e.g., ChR2) of light-sensitive transgenic cells 355. Additional LED 375 may be used to stimulate a second targeted ion channel or pump (e.g., NpHR). Yet another LED 380 may be used to stimulate a voltage sensitive dye (e.g. RH1691 or calcium dye, such as Fura-2). Each LED may be arranged to output specific wavelengths and intensities for stimulus of respective targeted compounds. In one instance, an LED may affect more than one target, depending upon the specific sensitivities of each compound used. Photodiode 365 detects the fluorescence of a selected voltage dye, while photodiode 370 is sensitive to the spectrum fluoresced by a selected calcium dye. The use of multiple LEDs for the same cell allows for the stimulation of LEIAs at different wavelengths. Multiple LEDs may also be used to detect different light wavelengths emitted by the LEIA.

FIG. 4A depicts an electronic circuit mechanism for activating the LED emitters used within the emitter/detector units, according to an example embodiment of the invention. Control device 401 generates a "light on signal" 402 to transistor base 405. This "light on signal" 402 will remain on for the duration of a light flash desired, or alternatively may turn on and off in order to produce rhythmic light flashes at a specified frequency. Light on signal 402 permits (conventional) current to flow from power source 410, through resister 411, and through transistor collector 407 and transistor emitter 412, to ground 413. Current is also thereby permitted to pass through resistor 415, and into LED 420. LED 420 emits light 421, which falls upon well 425. In a particular instance, the transistor functions as transconductance amplifier of signal 402. In this manner, light of the appropriate wavelength, intensity and frequency is delivered to cells within the well 425, so as to cause them to stimulate the particular ion channel (e.g., ChR2) or pump (e.g., NpHR), or other photoactive membrane structure being used to regulate the activity of electrically excitable cells. Various other circuits are also possible. For example, other circuits can be used in place of circuit 406 to control LED 420 including, but not limited to, replacing the transistor with an operational amplifier, a field-effect-transistor, a resistor divider network, transistor-transistor logic, push-pull driver circuits and switches.

FIG. 4B depicts an example electronic circuit mechanism for light detection by the emitter/detector units, according to one embodiment of the invention. Control device 450 may (optionally, depending upon specific implementation) provide power to photodiode 455. Photodiode 455 receives fluoresced (emitted) light 456 from the LEIA on the cells within well 457. The received light results in an output signal. This output passes through resistor 460, and is input to Schmitt triggered hex inverter 470, which conditions the signal, providing a clean "high" or "low value" to be input to computer 450.

Operation of the photodetector is shown in photovoltaic mode, but the element may also be used in the photoconductive mode of operation. Of course, many other light-detection devices and methods may also be used, including phototransistors, photothyristors, and charged-coupled device (CCD) elements, or arrays of elements.

Alternatively, the 4B circuit can be used without Schmitt-triggered hex inverter 470, permitting a continuum of signal intensities to be transmitted directly to an analog input to computer 450 or to an analog-to-digital converter. Various other signal conditioning circuits are also possible.

Figure 4:
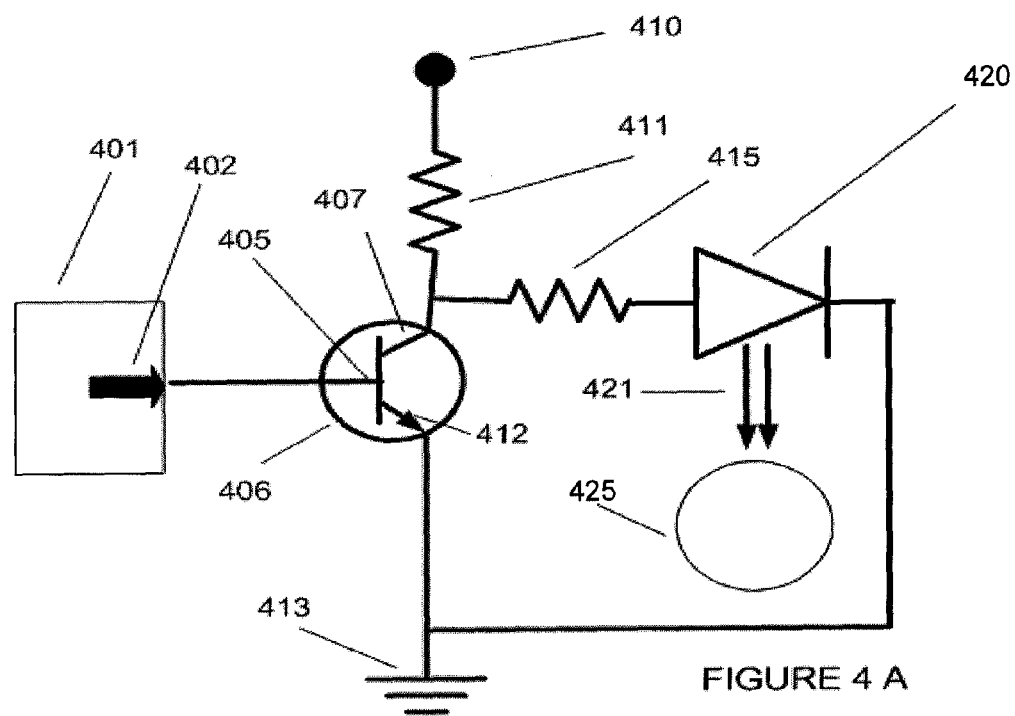
FIG. 4A depicts an electronic circuit mechanism for activating the LED emitters used within the emitter/detector units, according to an example embodiment of the present invention.
FIG. 4B depicts an electronic circuit mechanism for light detection by the emitter/detector units, according to an example embodiment of the present invention.
Figure 4:
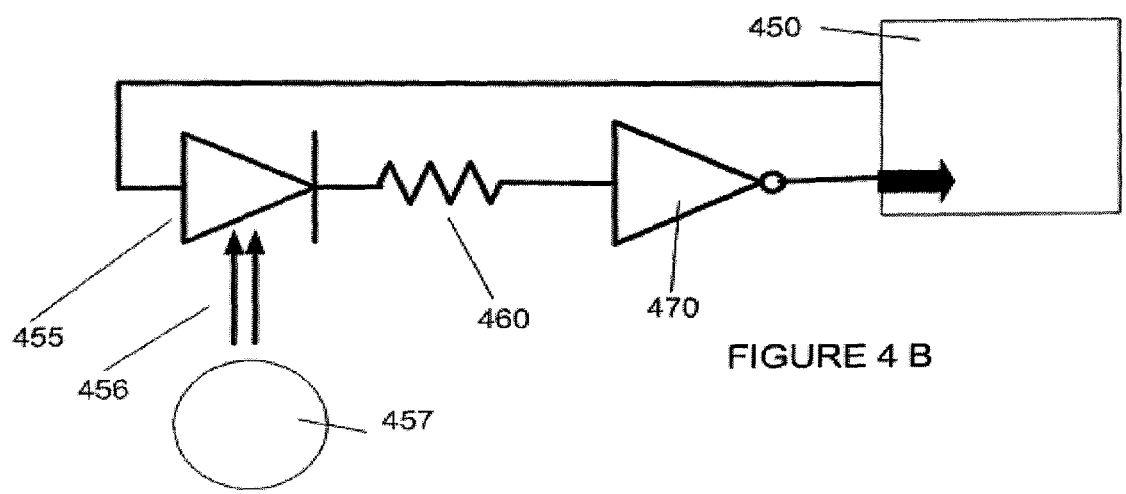
Figure 5:
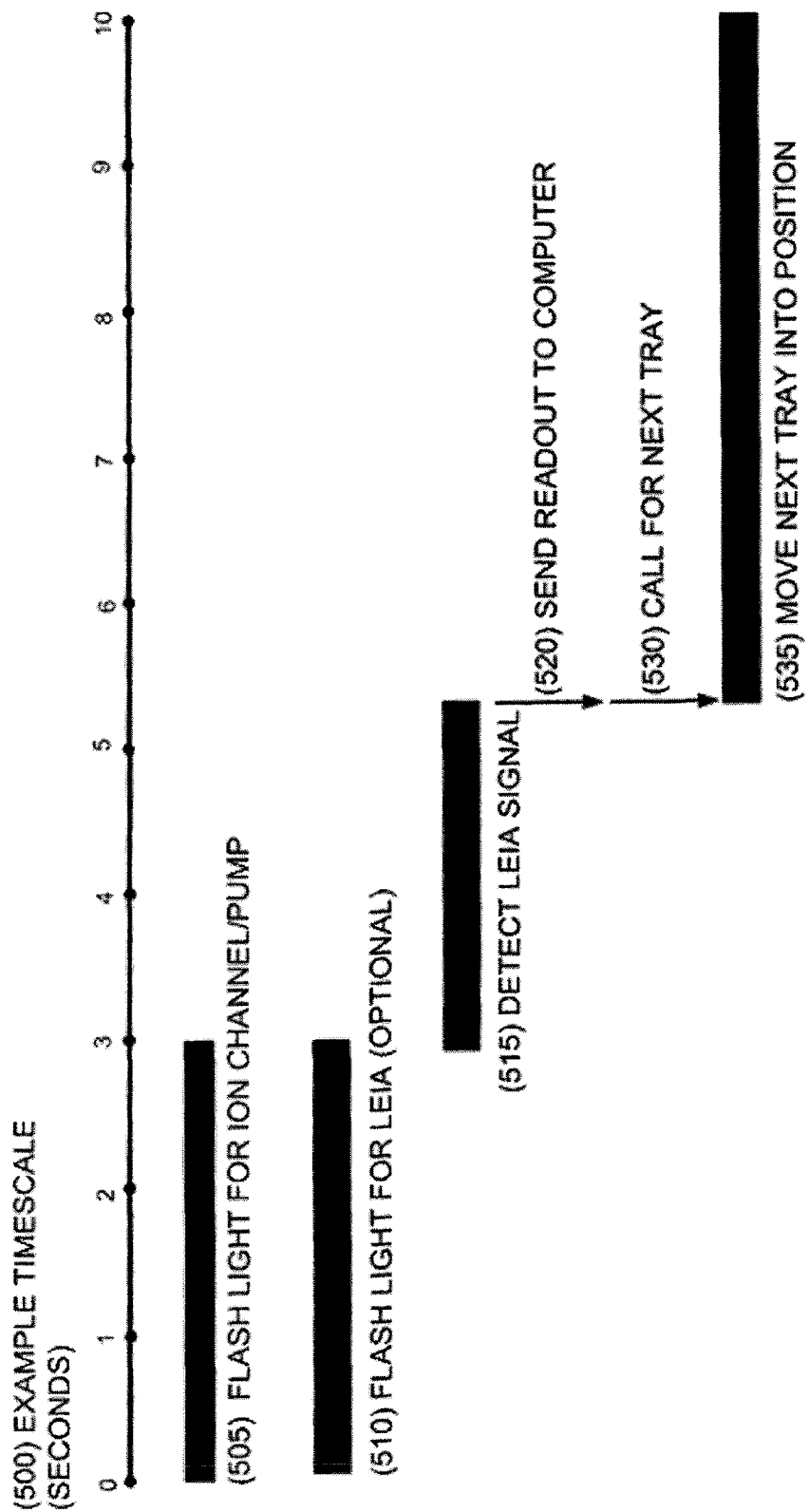
FIG. 5 shows a timeline for a sequence of events in the context of an example screening process, according to an example embodiment of the present invention.

FIG. 5 shows a sequence of steps using the embodiment shown in FIGS. 2, 3 and 4, in the context of projected high-throughput process time course 500 and in accordance with one embodiment of the invention. In step 505, light of the appropriate wavelength and intensity for the targeted ion channel is flashed—in this case for approximately 3 seconds. Concurrently, a LEIA stimulation flash 510 may optionally be triggered, depending upon the specific voltage or calcium dye, etc. being used. This LEIA compound may have been previously added to the well, or may be (artificially) genetically imparted upon the cells such that the chemical is produced/expressed by the cells. In step 515, the light signal produced by the LEIA is detected by the photodetector element (e.g. photodiode). For example, RH1691 fluoresces red light at about 70 nm.

In step 520, the signal resulting from the impingement of light onto the photodetector element is sent back to the computer. This may be a binary (e.g. "high" versus "low" signal intensity), or may be graded to reflect a continuum of activation levels. In the case that multiple photodetectors are used to determine energies at different wavelengths, the individual readings of these photodetectors may be logged in parallel or in sequence for appropriate interpretation in a later stage of the automated process. In step 530, the system calls for the next tray to be placed by the automated system. The next tray is moved into position at step 535 and the process may be repeated until all trays in a batch have been processed.

The level of light fluoresced is typically much lower than that required to optically stimulate a cell via light-sensitive ion channels or pumps. For example, ChR2 may require blue light of 1-10 mW/mm2 or more in order to robustly depolarize cells. RH 1691 may require approximately 0.1 mW/mm2 to stimulate it. Given that RH1691 shows significant sensitivity to blue light, (peak sensitivity is at the blue-green wavelengths), RH1691 is adequately stimulated by the same pulse used to stimulate ChR2, but emits light upon depolarization at a power of only on the order of 0.001 mW/mm2. This small amount of output light would be difficult to distinguish from the comparatively massive blue pulse used to stimulate ChR2, even if efficient filters were used in front of the detectors. Fortunately, temporal differences between the ChR2 stimulation (with simultaneous LEIA stimulation), and the fluorescent output of depolarized cells can be used to distinguish the light sources. For instance, the dye-based fluorescence may continue for a few seconds after the delivery of the depolarization pulse and the resultant action potential. Thus in some instances, such as a non-fluorescent LEIA or a luminescent activity dye, a separate stimulation flash is not required.

The amount of time allotted for light delivery may vary, and depends on factors including the level of light-gated ion channel/pump expression, and the density and characteristics of other ionic channel characteristics of that cell population. The amount of time allotted for light receipt may vary, and depends upon factors including the degree of accuracy required for the screening session. The amount of time allotted for well-plate (tray) changing may vary, and depends upon factors including the mechanical speed of the automated apparatus. If fast neurons are used as the cells being tested, the cellular stimulation and LEIA detection process may be accomplished in milliseconds.

In an example process, a 293T cell line expressing TASK-1 (to simulate the natural hyperpolarized membrane potential of neurons), ChR2 (to induce depolarization of the cell membrane), and the L-type calcium channel are used. Whole-cell patch clamping experiments show that the membrane of the modified 293T cell line is hyperpolarized to the point where the L-type calcium channels are closed. The cells are stimulated for 5 seconds with continuous blue light (470 nm) to activate ChR2. ChR2-mediated depolarization opens the co-expressed voltage-gated calcium channels. Upon ChR2 illumination, a strong calcium influx is recorded using a genetically-encoded calcium dye indicator, which fluoresced light with cellular depolarization. Nimodopine, a well-known L-type calcium channel blocker, abolishes the calcium influx—and hence the fluoresced signal when applied to the cells for 10 minutes. This data demonstrates the effectiveness of the system described herein.

The process above may be repeated under varying conditions. For example, a given set of cells may be tested with no drug present, and subsequently with one or more drugs present. The response of electrically-excitable cells under those conditions may be thereby documented, compared and studied. If the invention is implemented with at least one emitter/detector for each well on a tray and at least two concurrently operating devices, continuous operation may be maintained for extended periods of time.

Figure 6:
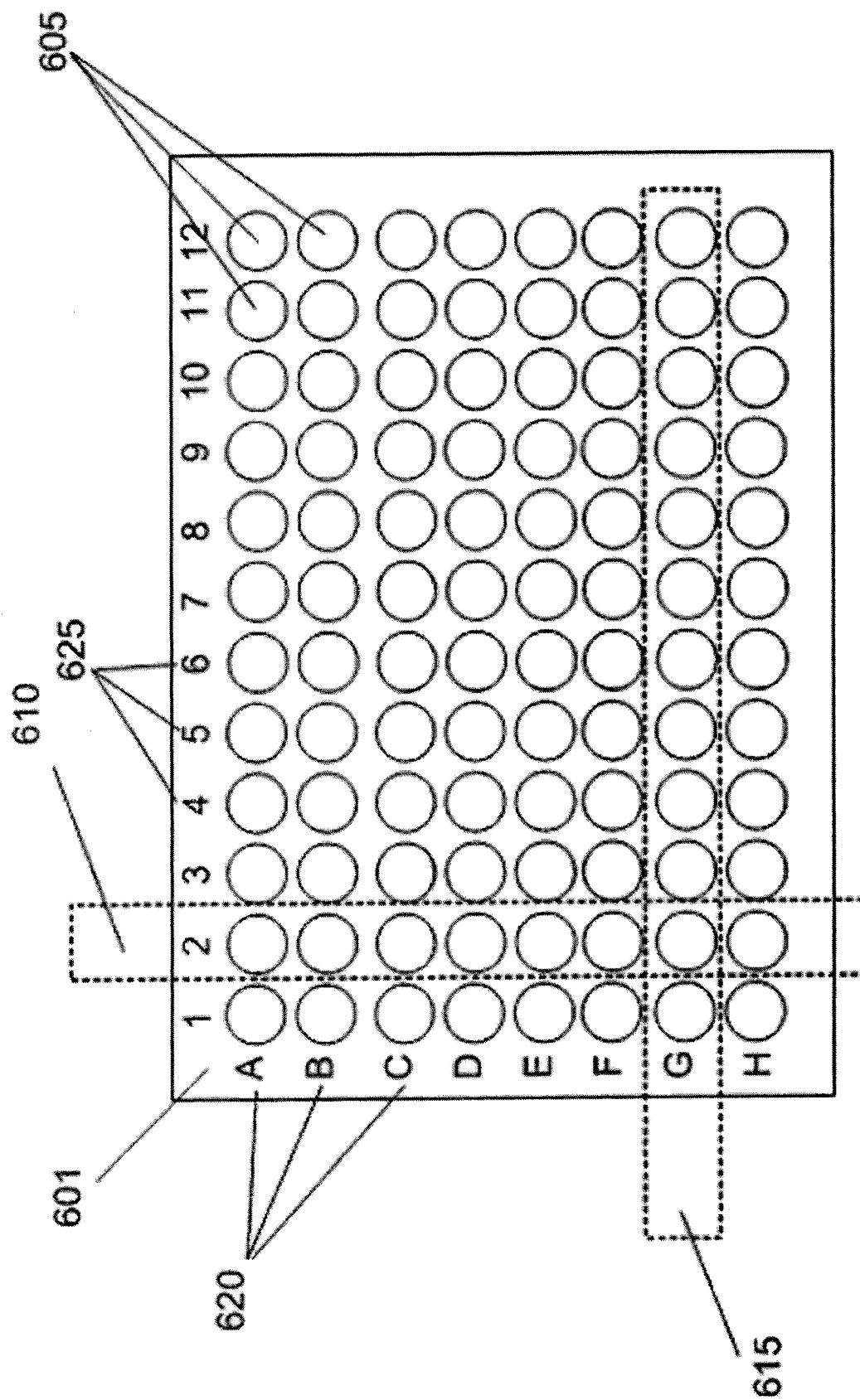
FIG. 6 illustrates an example of a layout of cell and drug samples within the wells of a well-plate, according to an example embodiment of the present invention.

FIG. 6 illustrates an example of a layout of cell and drug samples within the wells of a well-plate which is suitable for use within an embodiment of the invention. In this figure, well-plate 601 (also referred to herein as a "tray" contains wells 605 (examples), which are organized into columns 625, labeled with numbers 1-12 and rows 620, labeled with letters A-H. More specifically, an example column and row are defined by 610 and 615 respectively.

As an example of a functional layout of contents introduced into these wells, rows A-H of a single plate might be used for the testing of two different drugs. To represent a baseline condition, column 1 might contain optically gated cells, an endogenous or exogenous LEIA, but no drug. Columns 2-6 might be used for five different concentrations of Drug X, one concentration level per column. Likewise, columns 7-11 might be use for five different concentrations of Drug Y, one concentration per column. Column 12, while fully usable, is left unused in this particular example.

Variables in the various wells might include the type of cell being tested, the type of ion channel being tested for, the type of drug placed in the cell, the concentration of the drug placed in the well, the specific LEIA used, and the optical gating stimulation parameters (e.g. wavelength, intensity, frequency, duration) applied to the cells in that well.

Figure 7:
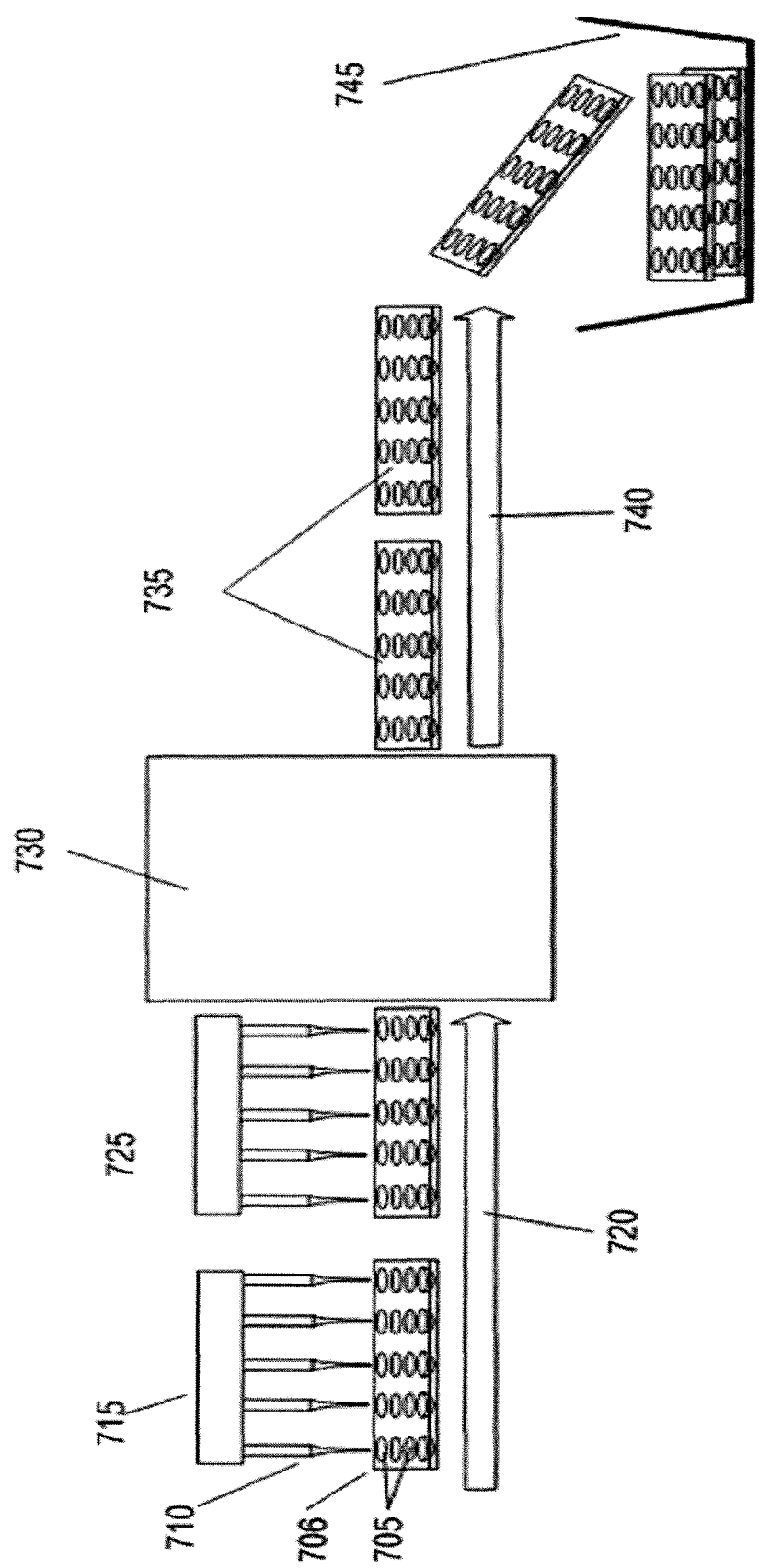
FIG. 7 illustrates the context in which the disclosed invention may be employed within a larger system that facilitates high-throughput drug screening, according to an example embodiment of the present invention.

FIG. 7 illustrates the context in which the disclosed invention may be employed within a larger system which facilitates high-throughput drug screening. Well-plate 706 contains wells 705. These are carried forward by conveyer 720, which may be a device such as a conveyor belt, robotic transporter or other delivery mechanism. Pipettes 710 are held in array by robotic member 715, and serve to inject the proper number of cultured cells and media into wells 705. Subsequently, well-plate 706 is moved down conveyer 720, where robotic member 725, analogous to robotic member 715 and also containing pipettes, injects the proper amount of a LEIA into wells 705. Conveyer 720 then brings well-plate 705 into screening chamber 730. An emitter/detector apparatus, such as those described in connection with FIG. 2, FIG. 3A, FIG. 3B, FIG. 4A, and FIG. 4B, is located within chamber 730. Additionally, portions of the processes described in FIG. 5 may occur within this chamber. Subsequently, well-plates 735 is moved out of screening chamber 730 by conveyor 740, and discarded at 745. In an alternative embodiment, one or more robotic devices may move pipettes 710, screening chamber 730, etc. to the locations of well-plate 706, rather than vice-versa.

Consistent with the above discussion, example screening methods could include the collection of multiple data points without having to switch samples. Because control over the samples is reversible in the same sample preparation by simply turning the activating light on and off with fast shutters, the same samples can be reused. Further, a range of patterns of stimulation can be provided to the same cell sample so that testing can be performed for the effect of drugs without concern with regards to differences across different sample preparations. By modulating the level of excitation (e.g., by ramping the level from no light to a high or maximum intensity), the effect of the drug across a range of membrane potentials can be tested. This permits for the identification of drugs that are efficacious during hyperpolarized, natural, or depolarized membrane potentials.

The cell lines described herein may be a particularly useful for detailed characterization of drug candidates in a high-throughput manner. Optical control is relatively fast, thereby allowing for the testing the drug's activity under more physiological forms of activation. For example, different frequencies of depolarization and/or hyperpolarization may be used to determine how a drug interacts with the channel under physiological forms of neural activity. In some instances, the process may be accomplished without the application of expensive chemical dyes to the cell lines.

In conjunction with the various properties discussed herein, the use of various embodiments of the invention may be particularly useful for improving screening throughput by eliminating the need for cumbersome mechanical manipulation and liquid handling. Various embodiments may also be useful for repeatable the screening assay using the same samples, reducing screening cost by eliminating the need for chemically-based fluorescence reports, producing high temporal precision and low signal artifact (due to the optical nature of the voltage manipulation), modulating the level of depolarization by attenuating the light intensity used for stimulation, and ascertaining the kinetics of the drug's modulation on the ion channel through the use of pulsed light patterns.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use of digital logic or microprocessors to control the emitted light. Such modifications and changes do not depart from the true spirit and scope of the present invention, which is set forth in the following claims.

What is claimed is:

1. A method for screening test drugs to identify their effects on cell membrane voltage-gated ion channel, the method comprising: a) contacting a mammalian cell with a test drug, wherein the cell: is genetically modified to express a heterologous, microbial light-responsive ChR2 ion channel comprising an amino acid sequence having at least 75% amino acid sequence identity to SEQ ID NO: 1, wherein the heterologous ChR2 ion channel, when activated by light, results in a change in the voltage in the cell membrane; wherein the cell comprises: i) a voltage-gated ion channel that causes a change in the intracellular concentration of an ion in response to the light-induced change in voltage; and ii) an indicator that produces a fluorescent signal in response to a change in the intracellular concentration of the ion; b) activating the heterologous, microbial light responsive ChR2 ion channel with light; c) detecting a fluorescent signal produced by the indicator; processing data received from the indicator; and storing the processed data received from the indicator, wherein a change in the signal produced by the indicator in the presence of the test drug, compared to the signal produced in the absence of the test drug, indicates that the test drug is a candidate drug that affects the voltage-gated ion channel.

2. The method of claim 1, wherein the voltage-gated ion channel is a $Ca^{2+}$ channel, a $K^+$ channel, a $Cl^-$ channel, or a $Na^+$ channel.

3. The method of claim 1, wherein the voltage-gated ion channel is a $Ca^{2+}$ channel, and wherein the fluorescence producing indicator is a calcium-sensitive dye.

4. The method of claim 1, further comprising introducing a plurality of test drugs to respective wells of an array of wells that each contain the mammalian cells and detecting light from respective wells from the array of wells using an array of optical sensors for detecting light.

5. The method of claim 1, wherein the light-responsive ChR2 ion channel comprises an amino acid sequence having at least 85% amino acid sequence identity to SEQ ID NO:1.

6. The method of claim 1, wherein the light-responsive ChR2 ion channel comprises an amino acid sequence having at least 90% amino acid sequence identity to SEQ ID NO:1.

7. The method of claim 1, wherein the light-responsive ChR2 ion channel comprises an amino acid sequence having at least 95% amino acid sequence identity to SEQ ID NO:1.

8. The method of claim 1, wherein the cell is an immortalized cell line.

9. The method of claim 1, wherein the indicator is a voltage-sensitive dye.

10. A method for screening test drugs to identify their effects on cell membrane voltage-gated ion channel, the method comprising:
a) contacting a mammalian cell with a test drug, wherein the cell is genetically modified to express a heterologous, microbial light-responsive ion channel and a heterologous, microbial light-responsive ion pump that, when activated by light, results in a change in the voltage in the cell membrane; wherein the cell comprises:
i) a voltage-gated ion channel that causes a change in the intracellular concentration of an ion in response to the light-induced change in voltage; and
ii) an indicator that produces a fluorescent signal in response to a change in the intracellular concentration of the ion;
b) activating the heterologous, microbial light responsive ion channel or heterologous, microbial light-responsive ion pump with light;
c) detecting a fluorescent signal produced by the indicator; processing data received from the indicator; and storing the processed data received from the indicator, wherein a change in the signal produced by the indicator in the presence of the test drug, compared to the signal produced in the absence of the test drug, indicates that the test drug is a candidate drug that affects the voltage-gated ion channel.

11. The method of claim 10, wherein the light-responsive ion channel is a ChR2 ion channel comprising an amino acid sequence having at least 75% amino acid sequence identity to SEQ ID NO:1.

12. The method of claim 10, wherein the light-responsive ion pump is an NpHR ion pump.

13. The method of claim 10, wherein the voltage-gated ion channel is a $Ca^{2+}$ channel, a $K^+$ channel, a $Cl^-$ channel, or a $Na^+$ channel.

14. The method of claim 10, wherein the voltage-gated ion channel is a $Ca^{2+}$ channel, and wherein the fluorescence producing indicator is a calcium-sensitive dye.

15. The method of claim 10, wherein the light-responsive ion channel is a ChR2 ion channel comprising an amino acid sequence having at least 85% amino acid sequence identity to SEQ ID NO:1.

16. The method of claim 10, wherein the light-responsive ion channel is a ChR2 ion channel comprising an amino acid sequence having at least 90% amino acid sequence identity to SEQ ID NO:1.

17. The method of claim 10, wherein the light-responsive ion channel is a ChR2 ion channel comprising an amino acid sequence having at least 95% amino acid sequence identity to SEQ ID NO:1.

18. The method of claim 10, wherein the cell is an immortalized cell line.

19. The method of claim 10, wherein the indicator is a voltage-sensitive dye.

* * * * *